United States Patent
Shigemoto

(10) Patent No.: US 9,618,502 B2
(45) Date of Patent: Apr. 11, 2017

(54) MUSCLE STEM CELL OR MYOBLAST, METHOD FOR SCREENING SUBSTANCES THAT PARTICIPATE IN METABOLIC CONVERSION USING SAME, AND PHARMACEUTICAL COMPOSITION COMPRISING SUBSTANCE OBTAINED FROM SAID SCREENING METHOD

(71) Applicant: TOKYO METROPOLITAN GERIATRIC HOSPITAL AND INSTITUTE OF GERONTOLOGY, Tokyo (JP)

(72) Inventor: Kazuhiro Shigemoto, Tokyo (JP)

(73) Assignee: Tokyo Metropolitan Geriatric Hospital and Institute of Gerontology, Tokyo (JP)

( * ) Notice: Subject to any disclaimer, the term of this patent is extended or adjusted under 35 U.S.C. 154(b) by 0 days.

(21) Appl. No.: 15/031,491

(22) PCT Filed: Oct. 24, 2014

(86) PCT No.: PCT/JP2014/078366
§ 371 (c)(1),
(2) Date: Jul. 1, 2016

(87) PCT Pub. No.: WO2015/060430
PCT Pub. Date: Apr. 30, 2015

(65) Prior Publication Data
US 2016/0305933 A1      Oct. 20, 2016

(30) Foreign Application Priority Data
Oct. 24, 2013   (JP) ................. 2013-221037

(51) Int. Cl.
G01N 33/50      (2006.01)
A61K 31/436     (2006.01)
A61K 45/06      (2006.01)
A61K 31/198     (2006.01)
A61K 31/36      (2006.01)
A61K 38/18      (2006.01)
A61K 38/20      (2006.01)
A61K 38/00      (2006.01)

(52) U.S. Cl.
CPC ....... *G01N 33/5061* (2013.01); *A61K 31/198* (2013.01); *A61K 31/36* (2013.01); *A61K 31/436* (2013.01); *A61K 38/1825* (2013.01); *A61K 38/2086* (2013.01); *A61K 45/06* (2013.01); *G01N 33/5023* (2013.01); *A61K 38/00* (2013.01); *G01N 2500/10* (2013.01)

(58) Field of Classification Search
CPC .................... C07K 14/4716; G01N 33/6887
See application file for complete search history.

(56) References Cited

U.S. PATENT DOCUMENTS

2010/0215657 A1   8/2010  Glass et al.

FOREIGN PATENT DOCUMENTS

| JP | 2007528755 A  | 10/2007 |
| JP | 2010535828 A  | 11/2010 |
| JP | 2011510620 A  | 4/2011 |
| WO | 2005116194 A  | 12/2005 |
| WO | 2013116691 A1 | 8/2013 |

OTHER PUBLICATIONS

Dulyaninova et al. 2007; Myosin-IIA heavy-chain phosphorylation regulates the motility of MDA-MB231 carcinoma cells. Molecular Biology of the Cell. 18: 3144-3155.*
Pandya et al. 2006; Fibrosis, not cell size, delineates _-myosin heavy chain reexpression during cardiac hypertrophy and normal aging in vivo. PNAS 103(45): 16864-16869.*
Goncalves et al. 2008; Genetic complementation of human muscle cells via directed stem cell fusion. Molecular Therapy. 16(4): 741-748.*
Extended European Search Report; Reference 161159EP; Application No./Patent No. 14855049.4-1466/3061810PCT/JP2014078366, dated Feb. 9, 2016.
Eghtesad, S., et al; "Rapamycin ameliorates dystrophic phenotype in mdx mouse skeletal muscle," Mol. Med., Sep.-Oct. 2011, vol. 17 (9-10), p. 917-24.
Miniaci, M.C., et al; "CL316,243, a selective beta-3-adrenoceptor agonist, activates protein translation through mTOR/p70S6K signaling pathway in rat skeletal muscle cells," Pflugers Arch., Apr. 2013, vol. 465 (4), p. 509-16.
Park, I-H et al, "Mammalian target of rapamycin (mTOR) signaling is required for a late-stage fusion process during skeletal myotube maturation," J. Biol. Chem, Sep. 9, 2005, vol. 280 (36), pp. 32009-32017.
Wang, Q., et al; "Mutations in the motor domain modulate myosin activity and myofibril organization," J. Cell. Sci., Oct. 15, 2003, vol. 116 (pt 20), p. 4227-38.

(Continued)

*Primary Examiner* — Karen Cochrane Carlson
(74) *Attorney, Agent, or Firm* — Teige P. Sheehan; Heslin Rothenberg Farley & Mesiti PC

(57) ABSTRACT

The object of the present invention is to provide a method for screening a substance involved in a metabolic shift of skeletal muscle, and a kit for screening a substance involved in a metabolic shift of skeletal muscle.
The object can be solved by a muscle stem cell or myoblast comprising at least one myosin-heavy chain fusion gene selected from the group consisting of a myosin-heavy chain I fusion gene wherein a myosin-heavy chain I gene and a fluorescent protein or photoprotein gene are fused, a myosin-heavy chain IIa fusion gene wherein a myosin-heavy chain IIa gene and a fluorescent protein or photoprotein gene are fused, a myosin-heavy chain IId/x fusion gene wherein a myosin-heavy chain IId/x gene and a fluorescent protein or photoprotein gene are fused, and a myosin-heavy chain IIb fusion gene wherein a myosin-heavy chain IIb gene and a fluorescent protein or photoprotein gene are fused.

5 Claims, 5 Drawing Sheets

(56) References Cited

OTHER PUBLICATIONS

Ouchi, Noriyuki, "Kokkakukin Yurai Bunpitsu Inshi Myokine to Shikkan," Modem Physician, Nov. 2011, vol. 31 (11), pp. 1356-1358.
Lynch, G.S., "Novel therapies for sarcopenia: ameliorating age-related changes in skeletal muscle," Expert Opinion on Therapeutic Patents, Jan. 2002, vol. 12 (1), pp. 11-27.
International Search Report for PCT/JP2014/078366 dated Jan. 27, 2015.
Schaakxs, D., et al, "Regenerative cell injection in denervated muscle reduces atrophy and enhances recovery following nerve repair," Muscle & Nerve, May 2013, vol. 47, p. 691-701.
Castellani, C., et al, "The contribution of stem cell therapy to skeletal muscle remodeling in heart failure," International Journal of Cardiology, (2013), vol. 168, p. 2014-2021.
Mazzini, L., et al, "Transplantation of mesenchymal stem cells in ALS," Progress in Brain Research, (2012), vol. 201, p. 333-359.
Pandya, K., et al, "Fibrosis, not cell size, delineates beta-myosin heavy chain reexpression during cardiac hypertrophy and normal aging in vivo," Proceeding of the National Academy of the Sciences of the United States of America, (2006), vol. 103, p. 16864-16869.
Mori, S. et al, Grants for scientific, academic and medical research related to sports, Mizuno Sports Foundation, 2010, http://www.mizuno.co.jp/zaidan/ikagaku/josei_2010.html.
Office Action issued by the Japan Patent Office in Patent Application No. No. 2015-543925, mailed Jan. 31, 2017.

* cited by examiner (A)  (B)

(A)

(B)

A

B

SEQUENCE LISTING

<160> NUMBER OF SEQ ID NOS: 2

<210> SEQ ID NO 1
<211> LENGTH: 210
<212> TYPE: PRT
<213> ORGANISM: Mus musculus

<400> SEQUENCE: 1

```
Met Glu Trp Met Arg Ser Arg Val Gly Thr Leu Gly Leu Trp Val Arg
1               5                   10                  15

Leu Leu Leu Ala Val Phe Leu Leu Gly Val Tyr Gln Ala Tyr Pro Ile
                20                  25                  30

Pro Asp Ser Ser Pro Leu Leu Gln Phe Gly Gly Gln Val Arg Gln Arg
            35                  40                  45

Tyr Leu Tyr Thr Asp Asp Asp Gln Asp Thr Glu Ala His Leu Glu Ile
        50                  55                  60

Arg Glu Asp Gly Thr Val Val Gly Ala Ala His Arg Ser Pro Glu Ser
65                  70                  75                  80

Leu Leu Glu Leu Lys Ala Leu Lys Pro Gly Val Ile Gln Ile Leu Gly
                85                  90                  95

Val Lys Ala Ser Arg Phe Leu Cys Gln Gln Pro Asp Gly Ala Leu Tyr
            100                 105                 110

Gly Ser Pro His Phe Asp Pro Glu Ala Cys Ser Phe Arg Glu Leu Leu
        115                 120                 125

Leu Glu Asp Gly Tyr Asn Val Tyr Gln Ser Glu Ala His Gly Leu Pro
    130                 135                 140

Leu Arg Leu Pro Gln Lys Asp Ser Pro Asn Gln Asp Ala Thr Ser Trp
145                 150                 155                 160
```

```
Gly Pro Val Arg Phe Leu Pro Met Pro Gly Leu Leu His Glu Pro Gln
                165                 170                 175

Asp Gln Ala Gly Phe Leu Pro Pro Glu Pro Pro Asp Val Gly Ser Ser
            180                 185                 190

Asp Pro Leu Ser Met Val Glu Pro Leu Gln Gly Arg Ser Pro Ser Tyr
        195                 200                 205

Ala Ser
    210

<210> SEQ ID NO 2
<211> LENGTH: 209
<212> TYPE: PRT
<213> ORGANISM: Homo sapiens

<400> SEQUENCE: 2

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser
```

MUSCLE STEM CELL OR MYOBLAST, METHOD FOR SCREENING SUBSTANCES THAT PARTICIPATE IN METABOLIC CONVERSION USING SAME, AND PHARMACEUTICAL COMPOSITION COMPRISING SUBSTANCE OBTAINED FROM SAID SCREENING METHOD

CROSS REFERENCE TO RELATED APPLICATIONS

This application is a National Phase filing of International Application No. PCT/JP2014/078366, filed Oct. 24, 2014, which claims priority to Japanese Application No. 2013-221037, filed Oct. 24, 2013. The entire content of each prior application is hereby incorporated by reference.

TECHNICAL FIELD

The present invention relates to a muscle stem cell or myoblast, and a method for screening a substance involved in a metabolic shift using the same. According to the present invention, substances involved in a metabolic shift of skeletal muscle can be effectively screened.

BACKGROUND ART

We face a super-aged society today. Sarcopenia, as well as dementia, is a major problem in today's super-aged society, but an early diagnosis and prevention of muscle atrophy are long-standing problems. Sarcopenia is defined as a disease associated with a decrease in the amount of skeletal muscle. Further, in a broader sense, it is considered that sarcopenia includes a disease associated with a skeletal muscle weakness or a decline in function.

Sarcopenia is developed in skeletal muscles. The skeletal muscle is mainly composed of two fibers, i.e. slow-twitch muscle fiber and fast-twitch muscle fiber, and, in each muscle, these two fibers with a certain proportion are arranged in a mosaic-like arrangement. The slow-twitch muscle fiber has excellent, aerobic energy production ability. A contraction rate of the slow-twitch muscle fiber is low, but a tolerance to fatigue thereof is excellent. Therefore, it is considered that the slow-twitch muscle fiber is suitable for an exercise of endurance. On the other hand, the fast-twitch muscle fiber has excellent, anaerobic energy production ability, and a generated tension thereof is high. Therefore, it is considered that the fast-twitch muscle fiber is suitable for a resistance exercise.

Further, disuse muscle atrophy, motor nerve damage, cachexia, chronic obstructive lung disease, Crohn disease, type I and II diabetes, neuromuscular incurable disease, autoimmune myasthenia gravis, sarcopenic obesity, arteriosclerosis with muscle atrophy, muscle atrophy associated with cerebral vascular disease, muscle damage, muscle tissue reconstruction after external injury or surgery treatment, muscular dystrophy, or the like, is known as a disease with a change of skeletal muscle (non-patent literatures 1 to 3), and development of therapeutic agents against the above diseases have been conducted. However, an effective therapeutic agent has not been developed.

The incurable neuromuscular diseases include amyotrophic lateral sclerosis, polymyositis, Guillain-Barré syndrome, congenital myasthenia, muscular dystrophy, distal myopathy, congenital myopathy, glycogen storage disease, mitochondrial myopathy, steroid myopathy, inflammatory myopathy, endocrine myopathy, and lipid storage myopathy.

A MyHCβ-YFP knock-in mouse in which a fluorescent protein YFP is bound to myosin-heavy chain β is reported as a means for visualizing myosin-heavy chain β of a cardiac muscle (non-patent literature 4). The myosin-heavy chain β gene of a cardiac muscle is the same as a MyHCI gene of a skeletal muscle, and thus, the inventors have found that the MyHCI can be expressed in the skeletal muscle and visualized (non-patent literature 5). Hereinafter, MyHCβ-YFP is referred to as MyHCI-YFP. Further, the inventors prepared a knock-in mouse, wherein a fusion protein in which a fluorescent protein Sirius is bound to myosin-heavy chain IIa of a skeletal muscle, and a fusion protein in which a fluorescent protein mCherry is bound to myosin-heavy chain IIb of a skeletal muscle are knocked-in, and reported that a composition shift of muscle fibers caused by training can be visualized (non-patent literature 5). However, the knock-in mouse is not a model mouse of a skeletal muscle disease, and thus, it is not used for developing therapeutic agents.

CITATION LIST

Non-Patent Literature

[NON-PATENT LITERATURE 1] Muscle & Nerve, 2013, (the United state), vol. 47, p. 691-701
[NON-PATENT LITERATURE 2] International Journal of Cardiology), 2013, (the United state), vol. 168, p. 2014-21
[NON-PATENT LITERATURE 3] Progress in Brain Research, 2012, (the United state), vol. 201, p. 333-59
[NON-PATENT LITERATURE 4] Proceeding of the National Academy of Sciences of the United States of America, 2006, (the United state), vol. 103, p. 16864-9
[NON-PATENT LITERATURE 5] Shuich Mori, and three others, "Visualization of composition shift of muscle fibers by training using a biological imaging, ~Construction of novel model animal for research~" 2010, MIZUNO SPORTS PROMOTION FOUNDATION, Aid for scientific, academic, or madical study on sports [Search on Oct. 15, 2013], Internet, <http://www.mizuno.co.jp/zaidan/ikagaku/josei_2010.html>

SUMMARY OF INVENTION

Technical Problem

The object of the present invention is to provide a method for screening a substance involved in a metabolic shift of skeletal muscle. Further, another object of the present invention is to provide a therapeutic agent for sarcopenia or diseases with a change of skeletal muscle.

Solution to Problem

The inventors conducted intensive studies into a therapeutic agent for sarcopenia or diseases with a change of skeletal muscle, and as a result, to their surprise, found that candidates for therapeutic agents for sarcopenia or diseases with a change of skeletal muscle can be screened by screening candidate substances for treatment using muscle stem cells or myoblasts, wherein at least one myosin-heavy chain fusion gene selected from the group consisting of a myosin-heavy chain I fusion gene wherein a myosin-heavy chain I gene and a fluorescent protein or photoprotein gene are fused, a myosin-heavy chain IIa fusion gene wherein a myosin-heavy chain IIa gene and a fluorescent protein or photoprotein gene are fused, a myosin-heavy chain IId/x fusion gene wherein a myosin-heavy chain IId/x gene and a fluorescent protein or photoprotein gene are fused, and a myosin-heavy chain IIb fusion gene wherein a myosin-heavy chain IIb gene and a fluorescent protein or photoprotein gene are fused, are introduced.

The present invention is based on the above findings.

The present invention relates to

[1] a muscle stem cell or myoblast comprising at least one myosin-heavy chain fusion gene selected from the group consisting of a myosin-heavy chain I fusion gene wherein a myosin-heavy chain I gene and a fluorescent protein or photoprotein gene are fused, a myosin-heavy chain IIa fusion gene wherein a myosin-heavy chain IIa gene and a fluorescent protein or photoprotein gene are fused, a myosin-heavy chain IId/x fusion gene wherein a myosin-heavy chain IId/x gene and a fluorescent protein or photoprotein gene are fused, and a myosin-heavy chain IIb fusion gene wherein a myosin-heavy chain IIb gene and a fluorescent protein or photoprotein gene are fused,

[2] the muscle stem cell or myoblast of the item [1], wherein the cell is an immortalized cell,

[3] the muscle stem cell or myoblast of the item [1] or [2], wherein the fluorescent protein or photoprotein gene bound to a myosin-heavy chain I gene, the fluorescent protein or photoprotein gene bound to a myosin-heavy chain IIa gene, the fluorescent protein or photoprotein gene bound to a myosin-heavy chain IId/x gene, and the fluorescent protein or photoprotein gene bound to a myosin-heavy chain IIb gene are different from each other,

[4] the muscle stem cell or myoblast of any one of the items [1] to [3], wherein the fluorescent protein or photoprotein is at least one fluorescent protein or photoprotein selected from the group consisting of Sirius, EBFP, SBP2, EBP2, Azurite, mKalama1, TagBFP, mBlueberry, mTurquoise, ECFP, Cerulean, mCerulean, TagCFP, AmCyan, mTP1, MiCy (Midoriishi Cyan), TurboGFP, CFP, AcGFP, Tag-GFP, AG (Azami-Green), mAG1, ZsGreen, EmGFP (Emerald), EGFP, GP2, T-Sapphire, HyPer, TagYFP, mAmetrine, EYFP, YFP, Venus, Citrine, PhiYFP, PhiYFP-m, turboYFP, ZsYellow, mBanana, mKO1, KO (Kusabira Orange), mOrange, mOrange2, mKO2, Keima570, TurboRFP, DsRed-Express, DsRed, DsRed2, TagRFP, TagRFP-T, DsRed-Monomer, mApple, mRed2, mStrawberry, TurboFP602, mRP 1, JRed, KillerRed, mCherry, KeimaRed, HcRed, mRasberry, mKate2, TagFP635, mPlum, egFP650, Neptune, mNeptune, egFP670, and luciferase,

[5] a method for screening a substance involved in a metabolic shift, comprising the steps of: bringing muscle stem cells or myoblasts, of any one of the items [1] to [4], or inductively-differentiated myotube cells therefrom, into contact with a substance to be tested; and analyzing an expression of at least one myosin-heavy chain gene selected from the group consisting of a myosin-heavy chain I gene, a myosin-heavy chain IIa gene, a myosin-heavy chain IId/x gene, and a myosin-heavy chain IIb gene, in the cells

[6] the method for screening a substance involved in a metabolic shift of the item [5], wherein the expression analysis of a myosin-heavy chain gene is an analysis of an amount or proliferation of cells in which the fluorescent protein or photoprotein is expressed,

[7] the method for screening a substance involved in a metabolic shift of the item [5] or [6], wherein the substance involved in a metabolic shift is selected from the group consisting of an agent for treating or preventing disease associated with a decrease of slow-twitch muscle fibers, an agent for treating or preventing disease associated with an increase of in slow-twitch muscle fibers, an agent for treating or preventing disease associated with a decrease of fast-twitch muscle fibers, an agent for treating or preventing disease associated with an increase of fast-twitch muscle fibers, an anticancer drug, an immunosuppressive agent, and an agent for treating or preventing lifestyle-related diseases,

[8] a pharmaceutical composition for treating or preventing a disease associated with skeletal muscle weakness, muscle atrophy, or muscle damage, comprising rapamycin or a derivative thereof as an active ingredient,

[9] the pharmaceutical composition of the item [8], wherein the disease associated with skeletal muscle weakness, muscle atrophy, or muscle damage is disuse muscle atrophy, motor nerve damage, cachexia, chronic obstructive lung disease, Crohn disease, sarcopenic obesity, arteriosclerosis with muscle atrophy, muscle atrophy associated with cerebral vascular disease, or type I or type II diabetic amyotrophy,

[10] the pharmaceutical composition of the item [8], wherein the disease associated with skeletal muscle weakness, muscle atrophy, or muscle damage is muscle damage, external injury, muscular dystrophy, distal myopathy, congenital myopathy, glycogen storage disease, mitochondrial myopathy, steroid myopathy, inflammatory myopathy, endocrine myopathy, lipid storage myopathy, amyotrophic lateral sclerosis (ALS), disuse muscle atrophy, chronic cardiac failure, sarcopenia, autoimmune myasthenia gravis, polymyositis, dermatomyositis, inclusion body myositis, Guillain-Barré syndrome, congenital myasthenic syndrome, or muscle tissue reconstruction after surgery treatment, and the pharmaceutical composition is administered to a patient of the above diseases, in a transplantation therapy of mesenchymal stem cells, muscle stem cells, or myoblast,

[11] an inducer of differentiation of a cell having muscle stem cell differentiation capacity to a muscle stem cell, comprising rapamycin or a derivative thereof as an active ingredient,

[12] the inducer of differentiation of the item [11], wherein the cell having muscle stem cell differentiation capacity is mesenchymal stem cell, muscle stem cell, or myoblast,

[13] a pharmaceutical composition for treating or preventing a disease associated with skeletal muscle weakness, muscle atrophy, or muscle damage, comprising as an active ingredient, (1) a polypeptide consisting of the amino acid sequence of SEQ ID NO: 1 or SEQ ID NO: 2, i.e. fibroblast growth factor 21, or (2) a polypeptide having an amino acid sequence in which one or more amino acids are deleted, substituted, and/or added in an amino acid sequence of SEQ ID NO: 1 or SEQ ID NO: 2, and exhibiting a differentiation-inducing property of a cell having muscle stem cell differentiation capacity to a muscle stem cell,

[14] the pharmaceutical composition of the item [13], wherein the disease associated with skeletal muscle weakness, muscle atrophy, or muscle damage is disuse muscle atrophy, motor nerve damage, cachexia, chronic obstructive lung disease, Crohn disease, sarcopenic obesity, arteriosclerosis with muscle atrophy, muscle atrophy associated with cerebral vascular disease, or type I or type II diabetic amyotrophy,

[15] the pharmaceutical composition of the item [13], wherein the disease associated with skeletal muscle weakness, muscle atrophy, or muscle damage is muscle damage, external injury, muscular dystrophy, distal myopathy, congenital myopathy, glycogen storage disease, mitochondrial myopathy, steroid myopathy, inflammatory myopathy, endocrine myopathy, lipid storage myopathy, amyotrophic lateral sclerosis (ALS), disuse muscle atrophy, chronic cardiac failure, sarcopenia, autoimmune myasthenia gravis, polymyositis, dermatomyositis, inclusion body myositis, Guillain-Barré syndrome, congenital myasthenic syndrome, or muscle tissue reconstruction after surgery treatment, and the pharmaceutical composition is administered to a patient of the above diseases in a transplantation therapy of mesenchymal stem cells, muscle stem cells, or myoblasts,

[16] an inducer of differentiation of a cell having muscle stem cell differentiation capacity to a muscle stem cell, comprising as an active ingredient, (1) a polypeptide consisting of the amino acid sequence of SEQ ID NO: 1 or SEQ ID NO: 2, i.e. fibroblast growth factor 21, or (2) a polypeptide having an amino acid sequence in which one or more amino acids are deleted, substituted, and/or added in an amino acid sequence of SEQ ID NO: 1 or SEQ ID NO: 2, and exhibiting a differentiation-inducing property of a cell having muscle stem cell differentiation capacity to a muscle stem cell,

[17] the inducer of differentiation of the item [16], wherein the cell having muscle stem cell differentiation capacity is mesenchymal stem cell, muscle stem cell, or myoblast,

[18] a pharmaceutical composition for treating or preventing a disease associated with skeletal muscle weakness, muscle atrophy, or muscle damage, comprising a β3 receptor agonist or a derivative thereof as an active ingredient,

[19] the pharmaceutical composition of the item [18], wherein the disease associated with skeletal muscle weakness, muscle atrophy, or muscle damage is disuse muscle atrophy, motor nerve damage, cachexia, chronic obstructive lung disease, Crohn disease, sarcopenic obesity, arteriosclerosis with muscle atrophy, muscle atrophy associated with cerebral vascular disease, or type I or type II diabetic amyotrophy,

[20] the pharmaceutical composition of the item [18], wherein the disease associated with skeletal muscle weakness, muscle atrophy, or muscle damage is muscle damage, external injury, muscular dystrophy, distal myopathy, congenital myopathy, glycogen storage disease, mitochondrial myopathy, steroid myopathy, inflammatory myopathy, endocrine myopathy, lipid storage myopathy, amyotrophic lateral sclerosis (ALS), disuse muscle atrophy, chronic cardiac failure, sarcopenia, autoimmune myasthenia gravis, polymyositis, dermatomyositis, inclusion body myositis, Guillain-Barré syndrome, congenital myasthenic syndrome, or muscle tissue reconstruction after surgery treatment, and the pharmaceutical composition is administered to a patient of the above diseases, in a transplantation therapy of mesenchymal stem cells, muscle stem cells, or myoblasts,

[21] an inducer of differentiation of a cell having muscle stem cell differentiation capacity to a muscle stem cell, comprising a β3 receptor agonist or a derivative thereof as an active ingredient, and

[22] the inducer of differentiation of the item [21], wherein the cell having muscle stem cell differentiation potency is mesenchymal stem cell, muscle stem cell, or myoblast. Further, the present specification discloses

[23] a kit for screening substance involved in a metabolic shift, comprising muscle stem cells or myoblasts, of any one of the items [1] to [4], or inductively-differentiated myotube cells therefrom,

[24] the kit for screening substance involved in a metabolic shift of the item [23], wherein the substance involved in a metabolic shift is selected from the group consisting of an agent for treating or preventing disease associated with a decrease of slow-twitch muscle fibers, an agent for treating or preventing disease associated with an increase of in slow-twitch muscle fibers, an agent for treating or preventing disease associated with a decrease of fast-twitch muscle fibers, an agent for treating or preventing disease associated with an increase of fast-twitch muscle fibers, an anticancer drug, an immunosuppressive agent, and an agent for treating or preventing lifestyle-related diseases,

[25] a use of muscle stem cells or myoblasts, of any one of the items [1] to [4], or inductively-differentiated myotube cells therefrom, for preparing a kit for screening substance involved in a metabolic shift,

[26] the use for preparing a kit for screening substance involved in a metabolic shift of the item [25], wherein the substance involved in a metabolic shift is selected from the group consisting of an agent for treating or preventing disease associated with a decrease of slow-twitch muscle fibers, an agent for treating or preventing disease associated with an increase of in slow-twitch muscle fibers, an agent for treating or preventing disease associated with a decrease of fast-twitch muscle fibers, an agent for treating or preventing disease associated with an increase of fast-twitch muscle fibers, an anticancer drug, an immunosuppressive agent, and an agent for treating or preventing lifestyle-related diseases,

[27] a use of muscle stem cells or myoblasts, of any one of the items [1] to [4], or inductively-differentiated myotube cells therefrom, as a screening tool for screening substance involved in a metabolic shift,

[28] the use as a screening tool for screening substance involved in a metabolic shift, wherein the substance involved in a metabolic shift is selected from the group consisting of an agent for treating or preventing disease associated with a decrease of slow-twitch muscle fibers, an agent for treating or preventing disease associated with an increase of in slow-twitch muscle fibers, an agent for treating or preventing disease associated with a decrease of fast-twitch muscle fibers, an agent for treating or preventing disease associated with an increase of fast-twitch muscle fibers, an anticancer drug, an immunosuppressive agent, and an agent for treating or preventing lifestyle-related diseases.

Advantageous Effects of Invention

According to the muscle stem cell or myoblast of the present invention, substances involved in metabolic shift of skeletal muscle can be screened. Further, the substances involved in metabolic shift of skeletal muscle include substances which can be used as a therapeutic agent for diseases with a change of skeletal muscle. Thus, therapeutic agents for such diseases may be developed using the same. Furthermore, according to the screening method of the present invention, genes and proteins involved in metabolic shift of skeletal muscle can be screened. Such genes and proteins may be used as a marker of disease. In addition, according to the screening method of the present invention, substances involved in metabolic shift other than skeletal muscle can also be screened. That is, an anticancer drug, an immunosuppressive agent, and an agent for treating or preventing lifestyle-related diseases can be screened.

Further, the pharmaceutical composition of the present invention can treat or prevent skeletal muscle weakness or disease with muscle atrophy.

DESCRIPTION OF EMBODIMENTS

[1] Muscle Stem Cell or Myoblast

Figure 1:
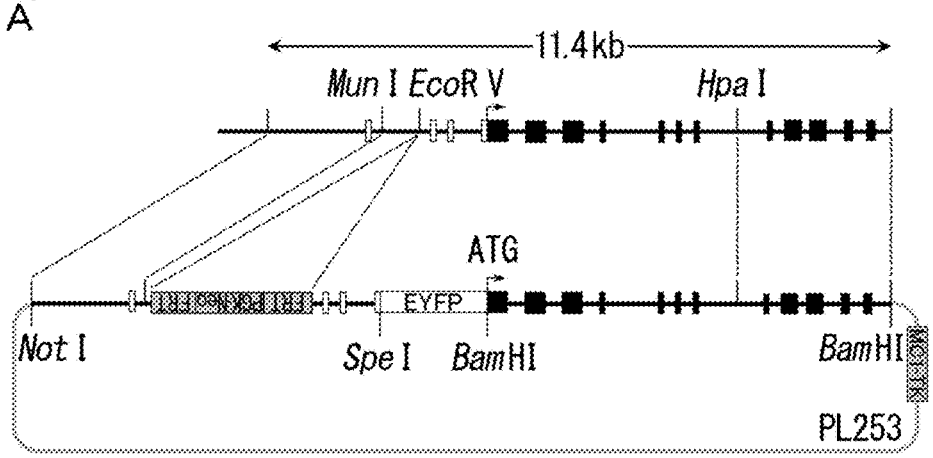
FIG. 1 is a set of views showing a targeting vector for introducing a myosin-heavy chain I gene and a fluorescent protein YFP (A), a targeting vector for introducing a myosin-heavy chain IIa gene and a fluorescent protein Sirius (B), targeting vector for introducing a myosin-heavy chain IIb gene and a fluorescent protein mCherry (C), and a targeting vector for introducing a myosin-heavy chain IId/x gene and a fluorescent protein mCerulean (D).
Figure 1:
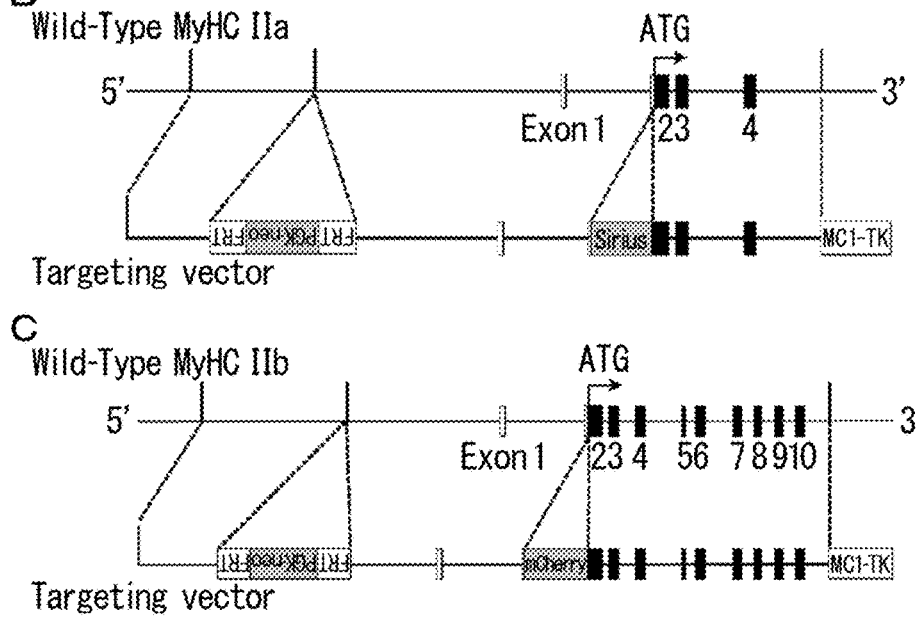
Figure 1:
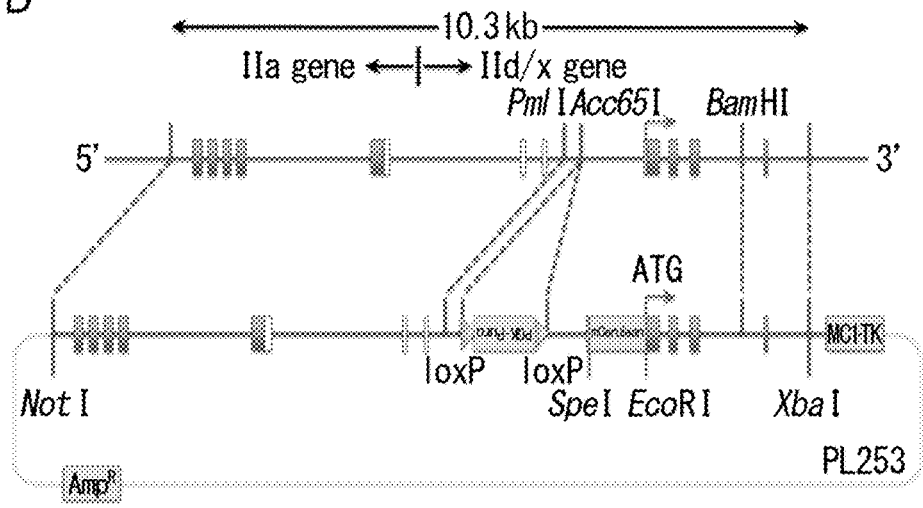

The muscle stem cell or myoblast of the present invention comprise at least one myosin-heavy chain fusion gene selected from the group consisting of a myosin-heavy chain I fusion gene wherein a myosin-heavy chain I gene and a fluorescent protein or photoprotein gene are fused, a myosin-heavy chain IIa fusion gene wherein a myosin-heavy chain IIa gene and a fluorescent protein or photoprotein gene are fused, a myosin-heavy chain IId/x fusion gene wherein a myosin-heavy chain IId/x gene and a fluorescent protein or photoprotein gene are fused, and a myosin-heavy chain IIb fusion gene wherein a myosin-heavy chain IIb gene and a fluorescent protein or photoprotein gene are fused.

(Knock-In Mouse, Transgenic Mouse)

The muscle stem cell or myoblast of the present invention is not limited, but can be obtained from a knock-in mouse wherein one or more genes selected from the group consisting of the myosin-heavy chain I fusion gene, myosin-heavy chain IIa fusion gene, myosin-heavy chain IId/x fusion gene, and myosin-heavy chain IIb fusion gene are knocked-in.

The above knock-in mouse may be prepared by known methods. In particular, a targeting vector for fusion protein is introduced to mouse ES cells, and an ES clone in which a homologous recombination is generated, is selected. Then, a chimeric mouse is prepared using the obtained ES clone, and offspring are obtained by crossbreeding the chimeric mouse with a normal mouse. The knock-in mouse can be obtained by selecting a mouse wherein the fusion protein gene is introduced to germ-line cells, from the offspring.

For example, a targeting vector containing a fusion gene wherein a myosin-heavy chain gene is bound to a fluorescent protein or photoprotein gene, can be constructed as follows. A genome sequence of a myosin-heavy chain gene of interest is sub cloned from a BAC library of male C57BL/6J mouse. On the other hand, a fluorescent protein or photoprotein gene can be obtained from a vector containing the same by PCR. The resulting fluorescent protein or photoprotein gene is inserted into a side of 5'-terminus of the myosin-heavy chain gene in frame of the translation initiation codon (ATG) thereof. The resulting targeting vector is made into a linear one and is introduced into mouse ES cells. A homologous recombinant ES clone is identified by PCR and southern blotting, and then a chimeric mouse is prepared by an aggregation method using the obtained ES. Then, offspring are obtained by crossbreeding the chimeric mouse with a male C57BL/6 mouse, and are subject to genotype determination. The knock-in mouse wherein the fusion gene in which a myosin-heavy chain gene is bound to a fluorescent protein or photoprotein gene is introduced, can be obtained by confirming the introduction of the fusion gene to germ-line cells.

The knock-in mouse may contain one or more fusion genes. That is to say, the knock-in mouse contains at least one myosin-heavy chain fusion gene selected from the group consisting of a myosin-heavy chain I fusion gene wherein a myosin-heavy chain I gene and a fluorescent protein or photoprotein gene are fused, a myosin-heavy chain IIa fusion gene wherein a myosin-heavy chain IIa gene and a fluorescent protein or photoprotein gene are fused, a myosin-heavy chain IId/x fusion gene wherein a myosin-heavy chain IId/x gene and a fluorescent protein or photoprotein gene are fused, and a myosin-heavy chain IIb fusion gene wherein a myosin-heavy chain IIb gene and a fluorescent protein or photoprotein gene are fused. However, the knock-in mouse containing the above four fusion genes is preferable.

Further, the muscle stem cell or myoblast of the present invention can be prepared from a transgenic mouse manufactured by introducing a fusion gene wherein a genomic gene of a promotor region of a myosin-heavy chain I gene, a myosin-heavy chain IIa gene, a myosin-heavy chain IId/x gene, or a myosin-heavy chain IIb gene, and a fluorescent protein or photoprotein gene are fused.

Furthermore, the knock-in mouse can be prepared by using a technique of artificial nuclease, i.e. ZFN (zinc-finger nuclease), or TALEN (transcription activator-like effector nuclease), or RNA guided type nuclease, i.e. CRISPR/Cas system (clustered regulatory interspaced short palindromic repeats, CRISPR-associated).

(Isolation of Muscle Stem Cell or Myoblast)

The muscle stem cell or myoblast of the present invention is not limited, but can be obtained from the knock-in mouse or the transgenic mouse through FACS (fluorescence activated cell sorting) as a satellite cell. Further, the muscle stem cell or myoblast of the present invention is not limited, but is preferably isolated from the knock-in mouse or transgenic mouse and is continuously cultivated.

Cells are obtained from skeletal muscles of the knock-in mouse or transgenic mouse by a collagenase treatment. The resulting cells are negatively selected using CD31, which is a marker of endothelial cells, CD45, which is a marker of hematopoietic cells, and Sca1, which is a marker of cells differentiating to fibroblasts and adipose cells. Subsequently, the resulting cells are positively selected using VCAM or SM/C-2.6, which is a marker of satellite cells, to thereby isolate muscle stem cells (satellite cells).

(Muscle Stem Cell or Myoblast)

The muscle stem cell or myoblast of the present invention may be used for the screening method of the present invention. That is, the screening method of the present invention can be performed using the primary culture cells isolated from the knock-in mouse or transgenic mouse by the above method. However, the muscle stem cell or myoblast of the present invention is not limited, but immortalized cells are preferable. If the muscle stem cell or myoblast is an immortalized cell, it is not necessary to isolate muscle stem cells or myoblasts from the knock-in mouse or transgenic mouse, in each experiment. That is to say, the muscle stem cells can be cultured long term, and thus can be rapidly and efficiently used in the screening method of the present invention.

(Muscle Stem Cell or Myoblast)

The immortalized muscle stem cell is not limited, but may be prepared by crossbreeding the knock-in mouse or transgenic mouse with an Immortmouse having H-2Kb-promoter induced by IFN-γ and temperature-sensitive SV40 large T antigen, as shown in the working examples. The immortalized cell is not the limit, but there are also proliferative passage cells, as shown in the working examples.

(Preparation of Muscle Stem Cell or Myoblast from Specimen other than Mouse)

The muscle stem cell or myoblast of the present invention can be prepared using the technique of ZFN system, TALEN system or CRISPR/Cas system. That is, the fluorescent protein gene or photoprotein gene may be inserted into a myosin-heavy chain I gene, a myosin-heavy chain IIa gene, a myosin-heavy chain IId/x gene, or a myosin-heavy chain IIb gene by the technique of ZFN system, TALEN system or CRISPR/Cas system. The muscle stem cell or myoblast of the present invention can be prepared thereby.

(Differentiation Induction)

Figure 2:
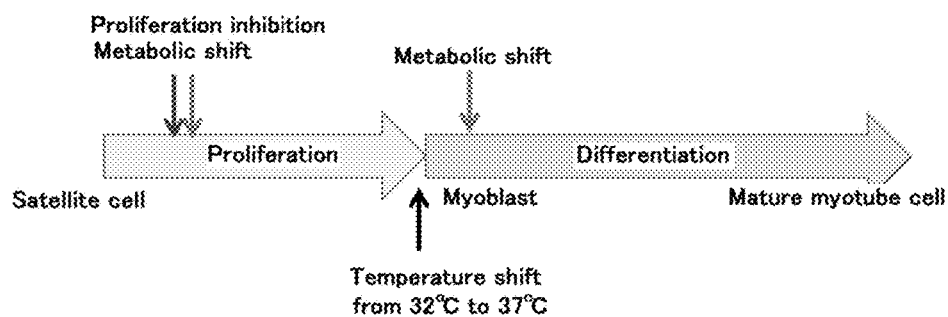
FIG. 2 is a view showing a differentiation induction of a muscle stem cell (satellite cell) to a myoblast and a myotube cell (differentiated muscle cell).

The muscle stem cell (satellite cell) of the present invention differentiates into a myoblast, and further differentiates into a myotube cell (muscle fiber cell) (FIG. 2).

The muscle stem cell and myoblast are proliferative cells. The myotube cell (muscle fiber cell) is a multinucleated cell wherein many myoblasts are fused together.

A differentiation induction of a muscle stem cell to a myoblast can be performed, but is not particularly limited, as follows. The muscle stem cells are continuously cultured in a cell culture medium (Dulbecco's modified Eagle's medium) with 10% fetal calf serum, and then the differentiation is induced by culturing the same using 2% horse serum instead of 10% fetal calf serum, at the differentiation induction.

Further, the differentiation induction of a myoblast to a myotube cell (muscle fiber cell) can be performed, but is not particularly limited, as follows. The myoblasts are differentiated to a myotube cell (muscle fiber cell) by culturing in a cell culture medium (Dulbecco's modified Eagle's medium) with 2% horse serum.

Furthermore, the immortalized cell obtained by being crossbred with the Immortmouse, can inductively-differentiate to a myoblast or a myotube cell (muscle fiber cell) by shifting the temperature from 32° C. to 37° C. and degrading a temperature-sensitive SV40 large T antigen.

The substance involved in the metabolic shift obtained by the screening method of the present invention can induce a differentiation to a specific muscle fiber cell, and can shorten the time of differentiation induction, compared with the differentiation induction to a myotube cell (muscle fiber cell) by horse serum, or the like.

The fluorescent protein gene contained in the fusion gene in the muscle stem cell or myoblast of the present invention is not particularly limited. For example, a gene coding a known fluorescent protein usually used in this field can be used. Specific examples of such fluorescent proteins are at least one blue fluorescent protein, such as Sirius, EBFP, SBP2, EBP2, Azurite, mKalama1, TagBFP, mBlueberry, mTurquoise, ECFP, Cerulean, mCerulean, TagCFP, AmCyan, mTP1, MiCy (Midoriishi Cyan), TurboGFP, CFP, AcGFP, TagGFP, AG (Azami-Green), mAG1, ZsGreen, EmGFP(Emerald), EGFP, GP2, T-Sapphire, or HyPer; yellow fluorescent protein, such as TagYFP, mAmetrine, EYFP, YFP, Venus, Citrine, PhiYFP, PhiYFP-m, turboYFP, ZsYellow, or mBanana; orange color fluorescent protein, such as mKO1, KO(Kusabira Orange), mOrange, mOrange2, or mKO2; red fluorescent protein, such as Keima570, TurboRFP, DsRed-Express, DsRed, DsRed2, TagRFP, TagRFP-T, DsRed-Monomer, mApple, AsRed2, mStrawberry, TurboFP602, mRP1, JRed, KillerRed, mCherry, KeimaRed, HcRed, mRasberry, mKate2, TagFP635, mPlum, egFP650, Neptune, mNeptune, or egFP670.

The photoprotein gene contained in the fusion gene in the muscle stem cell or myoblast of the present invention is not particularly limited. For example, a gene coding a known photoprotein usually used in this field can be used. A specific example of such a photoprotein is a luciferase, but the origin of the luciferase is not limited. For example, there may be mentioned firefly luciferase, sea firefly luciferase, bacterial luciferase, dinoflagellate genus luciferase, renilla luciferase or click beetle luciferase.

The fluorescent protein or photoprotein gene bound to the myosin-heavy chain I gene, the myosin-heavy chain IIa gene, the myosin-heavy chain IId/x gene, and the myosin-heavy chain IIb gene may be a gene coding the same fluorescent protein or photoprotein. For example, when the muscle stem cell or myoblast contains a single fusion gene, we have no problem using a gene coding the same fluorescent protein or photoprotein.

However, when the muscle stem cell or myoblast contains two or more fusion genes, it is preferable that the respective fluorescent protein genes and the like bound to myosin-heavy chains are different each other. A type of the myosin-heavy chain gene being expressed on the myotube cell (muscle fiber cell) can be identified by the colors of fluorescent proteins, and the like. In connection to this, the expression of the myosin-heavy chain genes may generally be identified by the colors of the fluorescent proteins and the like during the time from the late phase of myoblast to the differentiation induction phase of the myotube cell (muscle fiber cell).

[2] Method for Screening Substances Involved in Metabolic Shift

The method for a substance involved in a metabolic shift of the present invention comprises the steps of: bringing the above muscle stem cells or myoblasts, or inductively-differentiated myotube cells therefrom into contact with a substance to be tested; and analyzing an expression of at least one myosin-heavy chain gene selected from the group consisting of the myosin-heavy chain I gene, the myosin-heavy chain IIa gene, the myosin-heavy chain IId/x gene, and the myosin-heavy chain IIb gene, in the cells.

The biological cells shift the energy production efficiency (for example, a shift from glycolytic system to mitochondrial system, or a shift from mitochondrial system to glycolytic system), or the biosynthetic machinery (for example, a shift from anabolic reaction to a catabolic reaction, or a shift from catabolic reaction to anabolic reaction) for adapting cell proliferation, differentiation, inflammation reaction, stress, condition of the nutrition, unique function (such as, skeletal muscle, adipose cell, or Immunity). These conversions are referred to as the metabolic shift. The screening method of the present invention can select the substances involved in the metabolic shift.

(Contact Step)

In the contact step in the screening method of the present invention, the muscle stem cells or myoblasts, or the inductively-differentiated myotube cells therefrom, are brought into contact with substances to be tested.

The test substance is not particularly limited, so long as it may be involved in the metabolic shift or it is a library comprising the same. However, various known compounds (including peptides) registered in chemical files, compounds obtained by the combinatorial chemistry techniques [Terrett, N. K. et al., Tetrahedron, 51, 8135-8137 (1995)], or a group of random peptides prepared by employing a phage display method [Felici, F. et al., J. Mol. Biol., 222, 301-310 (1991)], low-molecular compounds, or the like, can be used. In addition, culture supernatants of microorganisms, culture supernatant of cells, body fluids, natural components derived from plants or marine organisms, or animal tissue extracts and the like may also be used as the test substance for screening.

The muscle stem cell differentiates into a myoblast, and further differentiates into a myotube cell by the stimulus of the differentiation induction. The cells are proliferated during the muscle stem cells and myoblasts, but the cells are not proliferated during the myotube cells.

A timing of contact of cells with test substances, i.e., a timing of addition of test substances, is not particularly limited. The muscle stem cells, myoblasts, or myotube cells in any stage may be used. If the test substance does not affect cell proliferation, the substances involved in metabolic shift may be screened in any stage of cells. However, if the test substance affects cell proliferation, it is preferable that the differentiated myoblasts or myotube cells are used.

For example, when the test substance is added to the muscle stem cells, the timing of addition of test substances is not limited, but it may be from a start of culture to 4 days after the start of culture, preferably from 1 to 3 days after the start of culture. When the test substance is added to the myoblasts or myotube cells, the timing of addition of test substances is not limited, but it may be from a start of differentiation induction to myoblast to 3 days thereafter, preferably 12 to 36 hours after the start of differentiation induction to the myoblast.

A concentration of a test substance may be optionally decided. However, it is considered that there may be an optimal concentration of the test substance for involving an effect on metabolic shift. Thus, it is preferable that the test substance diluted in a stepwise fashion is used.

A medium used in the contact step is not limited, so long as the muscle stem cell, myoblast, or myotube cell can be cultured, but there may be mentioned, for example, a cell culture medium (Dulbecco's modified Eagle's medium) with 10% fetal calf serum or 2% horse serum.

(Analysis Step)

In the analysis step of the present invention, expressions of one or more myosin-heavy chains selected from the group consisting of the myosin-heavy chain I gene, the myosin-heavy chain IIa gene, the myosin-heavy chain IId/x gene, and the myosin-heavy chain IIb gene are analyzed.

The analysis method of gene expression is not particularly limited, but includes, for example, an analysis method of mRNA amount, and an analysis method of protein amount translated from mRNA. As a detection method for mRNA expression, the known methods can be used. For example, there may be mentioned a northern blot method, a dot blot method, and a ribonuclease protection assay wherein the mRNA is directly measured, and an RT-PCR method such as a real time PCR method, a DNA microarray analysis, a DNA chip analysis, and a northern blot method wherein a cDNA is synthesized from mRNA and analyzed. However, the RT-PCR method, the DNA microarray analysis, and the DNA chip analysis are most preferable. Further, as the measuring method of the protein expression, there may be mentioned a western blotting method, a dot blotting method, a slot blotting method, or an enzyme-linked immunosorbent assay (ELISA). The expression level of fluorescent protein may be analyzed by the fluorescence or luminescence in this screening system, and therefore the expression level of fluorescent protein or photoprotein can be easily and accurately analyzed. That is to say, when a fluorescence level of a certain fluorescent protein is increased compared to a negative control in which a test substance is not added, it is determined that the cells which express a myosin-heavy chain with a certain fluorescent protein are increased. When a fluorescence level of a certain fluorescent protein is decreased, it is determined that the cells which express the myosin-heavy chain with a certain fluorescent protein are decreased. Further, when the number of myosin-heavy chain-expressed cells remains static and the fluorescence level of the fluorescent protein is increased or decreased, it is considered that the expression level of the myosin-heavy chain in a single cell is increased or decreased. That is, in the screening method of the present invention, substances involved in metabolic shift capable of increasing or decreasing the expression level of a myosin-heavy chain in a single cell, can be screened. The fluorescent protein level can be measured by, for example, a fluorescence microscope, a confocal laser microscope, or a multi-photon laser microscope.

Furthermore, the number of cells with the slow-twitch fiber wherein the myosin-heavy chain I is expressed, or the fast-twitch fiber wherein the myosin-heavy chain IIa, the myosin-heavy chain IId/x, or the myosin-heavy chain IIb is expressed, can be measured by counting the numbers of cells which express the each of the fluorescent proteins. Further, in place of the measurement of cell numbers, areas of cells which express the each muscle fiber can be calculated by measuring the fluorescence in a micrograph. Therefore, in the present specification, the number of cells and the area of cells are sometimes referred to as an "amount of cells" together. In addition, for example, the sentence that "an amount of cells which express myosin heavy chain I is increased" in a state without cell proliferation such as the state of a myotube cell, means that the cells are differentiated. Further, in the screening method of the present invention, the expression of a myosin-heavy chain in a single cell can be observed with time. Furthermore, the expressions of two or more myosin-heavy chains in a single cell can be observed. That is, the cell differentiation develops in each of the cells. In the screening method of the present invention, a change on a cellular level can be observed with time. This is because, in the present invention, the cell differentiation may be observed while culturing the cells. In an observation of the expression of a myosin-heavy chain using an antibody or the like, the intracellular myosin-heavy chain is stained, and thus, it is necessary to fix the cells. Therefore, it is difficult to observe the living cells with time.

For example, the muscle stem cell of the working Example contains the gene coding the fusion protein of the myosin-heavy chain I and fluorescent protein, YFP, the gene coding the fusion protein of the myosin-heavy chain IIa and fluorescent protein Sirius, the gene coding the fusion protein of the myosin-heavy chain IId/x and fluorescent protein Cerulean, and the gene coding the fusion protein of the myosin-heavy chain IIb and fluorescent protein Cherry.

Therefore, an increase and decrease of expression of the yellow YFP means an increase and decrease of expression of the myosin-heavy chain I protein (an increase and decrease of the number of cells which express the myosin-heavy chain I protein). The myosin-heavy chain I protein is expressed in the slow-twitch fiber, and is related to an oxidative metabolism (Table 1). The increase of the myosin-heavy chain I protein represents an increase of mitochondria amount, an enhancement of mitochondria function, an increase of amount of ATP production, an increase of fat metabolism or amino-acid metabolism.

In addition, test substances capable of increasing the myosin-heavy chain I protein is useful for treating or preventing diseases associated with muscle weakness, muscle atrophy, or muscle damage wherein the fast muscle is increased and the slow muscle is decreased. That is to say, they are effective for the treatment or prevention of the disease associated with increase of fast muscle and/or decrease of slow muscle. The test substances capable of increasing the myosin-heavy chain I can be used as a therapeutic agent for disuse muscle atrophy, motor nerve damage, cachexia, chronic obstructive lung disease, Crohn disease, sarcopenic obesity, arteriosclerosis with muscle atrophy, muscle atrophy associated with cerebral vascular disease, or type I or type II diabetic amyotrophy. In the above diseases, the slow muscle is decreased, and thus, the substances capable of increasing the myosin-heavy chain I protein, i.e., the substances capable of increasing cells with a myosin-heavy chain I protein, can be directly used as the agent for treating or preventing these diseases.

Furthermore, the test substances are useful for a selective therapeutic medicine for transplantation of mesenchymal stem cells, muscle stem cells, and/or myoblasts in a therapy of muscle damage, external injury, muscular dystrophy, distal myopathy, congenital myopathy, glycogen storage disease, mitochondrial myopathy, steroid myopathy, inflammatory myopathy, endocrine myopathy, lipid storage myopathy, amyotrophic lateral sclerosis (ALS), disuse muscle atrophy, chronic cardiac failure, sarcopenia, autoimmune myasthenia gravis, polymyositis, dermatomyositis, inclusion body myositis, Guillain-Barré syndrome, congenital myasthenia syndrome, or muscle tissue reconstruction after surgery treatment. The substance capable of increasing the myosin-heavy chain I protein may increase cells with the myosin-heavy chain I fiber. In the transplantation therapy, it is important that the slow-twitch fiber cells and the fast-twitch fiber cells are inductively-differentiated from mesenchymal stem cells, muscle stem cells, and/or myoblasts in a balanced manner. In connection to this, the substance capable of increasing the myosin-heavy chain I protein can be effectively used for the differentiation induction of muscle fiber cells due to the differentiation-inducing property of cells with the slow-twitch fiber.

The term "disease associated with muscle weakness" as used herein means disuse muscle atrophy, motor nerve damage, cachexia, chronic obstructive lung disease, Crohn disease, sarcopenic obesity, arteriosclerosis with muscle atrophy, muscle atrophy associated with cerebral vascular disease, type I or type II diabetic amyotrophy, muscle damage, distal myopathy, congenital myopathy, glycogen storage disease, mitochondrial myopathy, steroid myopathy, inflammatory myopathy, endocrine myopathy, lipid storage myopathy, amyotrophic lateral sclerosis (ALS), disuse muscle atrophy, chronic cardiac failure, sarcopenia, autoimmune myasthenia gravis, polymyositis, dermatomyositis, inclusion body myositis, Guillain-Barré syndrome, congenital myasthenia syndrome, muscular dystrophy, or muscle tissue reconstruction after surgery treatment.

Further, the term "disease associated with muscle atrophy" as used herein means disuse muscle atrophy, motor nerve damage, cachexia, chronic obstructive lung disease, Crohn disease, sarcopenic obesity, arteriosclerosis with muscle atrophy, muscle atrophy associated with cerebral vascular disease, type I or type II diabetic amyotrophy, muscle damage, distal myopathy, congenital myopathy, glycogen storage disease, mitochondrial myopathy, steroid myopathy, inflammatory myopathy, endocrine myopathy, lipid storage myopathy, amyotrophic lateral sclerosis (ALS), disuse muscle atrophy, chronic cardiac failure, sarcopenia, autoimmune myasthenia gravis, polymyositis, dermatomyositis, inclusion body myositis, Guillain-Barré syndrome, congenital myasthenia syndrome, muscular dystrophy, or muscle tissue reconstruction after surgery treatment.

Furthermore, the term "disease associated with muscle damage" as used herein means motor nerve damage, or external injury and muscle tissue reconstruction after surgery treatment.

Further, an increase and decrease of the blue Sirius means an increase and decrease of expression of the myosin-heavy chain IIa protein (an increase and decrease of the number of cells which express the myosin-heavy chain IIa protein). The myosin-heavy chain IIa protein is expressed in the fast-twitch fiber, and is related to an oxidative metabolism and glycolytic metabolism (Table 1). The increase of the myosin-heavy chain IIa protein represents an increase of mitochondria amount, an enhancement of mitochondria function, an increase of amount of ATP production, an increase of fat metabolism or amino-acid metabolism.

In addition, test substances capable of increasing the myosin-heavy chain IIa protein is useful for treating or preventing the disease associated with muscle weakness, muscle atrophy, or muscle damage wherein the fast muscle is increased and the slow muscle is decreased. That is to say, they are effective for the treatment or prevention of the disease associated with an increase of fast muscle and/or a decrease of slow muscle. The test substances capable of increasing the myosin-heavy chain IIa protein can be used as a therapeutic agent for disuse muscle atrophy, motor nerve damage, cachexia, chronic obstructive lung disease, Crohn disease, sarcopenic obesity, arteriosclerosis with muscle atrophy, muscle atrophy associated with cerebral vascular disease, or type I or type II diabetic amyotrophy. The substances capable of increasing the myosin-heavy chain IIa protein can be directly used as the agent for treating or preventing these diseases.

Furthermore, the test substances are useful for a selective, therapeutic transplantation of mesenchymal stem cells, muscle stem cells, and/or myoblasts for the purpose of treatment of muscle damage, distal myopathy, congenital myopathy, glycogen storage disease, mitochondrial myopathy, steroid myopathy, inflammatory myopathy, endocrine myopathy, lipid storage myopathy, amyotrophic lateral sclerosis (ALS), disuse muscle atrophy, chronic cardiac failure, sarcopenia, autoimmune myasthenia gravis, polymyositis, dermatomyositis, inclusion body myositis, Guillain-Barré syndrome, congenital myasthenia syndrome, muscular dystrophy, external injury or muscle tissue reconstruction after surgery treatment. The substance capable of increasing the myosin-heavy chain IIa protein may increase cells with the myosin-heavy chain IIa fiber. In the transplantation therapy, it is important that the slow-twitch fiber cells and the fast-twitch fiber cells are inductively-differentiated from mesenchymal stem cells, muscle stem cells, and/or myoblasts in a balanced manner. In connection to this, the substances capable of increasing the myosin-heavy chain IIa protein can be effectively used for the differentiation induction of cells with the myosin-heavy chain IIa fiber.

Further, an increase and decrease of the blue mCeruleans means an increase and decrease of expression of the myosin-heavy chain IId/x protein (an increase and decrease of the number of cells which express the myosin-heavy chain IId/x protein). The myosin-heavy chain IIa protein is expressed in the fast-twitch fiber, and is related to an oxidative metabolism and glycolytic metabolism (Table 1). The increase of the myosin-heavy chain IId/x protein represents an enhancement of glycometabolism function, and an increase of lipogenesis and amino-acids synthesis.

In addition, the test substances capable of increasing the myosin-heavy chain IId/x protein is useful for treating or preventing the disease associated with decrease of slow muscle. The test substances can be used as an agent for preventing or treating sarcopenia, or an agent for treating ALS.

Further, the test substances are useful for a selective, therapeutic transplantation of mesenchymal stem cells, muscle stem cells, and/or myoblasts for the purpose of treatment of muscle damage, distal myopathy, congenital myopathy, glycogen storage disease, mitochondrial myopathy, steroid myopathy, inflammatory myopathy, endocrine myopathy, lipid storage myopathy, amyotrophic lateral sclerosis (ALS), disuse muscle atrophy, chronic cardiac failure, sarcopenia, autoimmune myasthenia gravis, polymyositis, dermatomyositis, inclusion body myositis, Guillain-Barré syndrome, congenital myasthenia syndrome, muscular dystrophy, external injury or muscle tissue reconstruction after surgery treatment. The substance capable of increasing the myosin-heavy chain IId/x protein may increase cells with the myosin-heavy chain IId/x fiber. In the transplantation therapy, it is important that the slow-twitch fiber cells and the fast-twitch fiber cells are inductively-differentiated from mesenchymal stem cells, muscle stem cells, and/or myoblasts, according to a property of skeletal muscle of interest. In connection to this, the substances capable of increasing the myosin-heavy chain IId/x protein can be effectively used for the differentiation induction of cells with the myosin-heavy chain IId/x fiber.

Further, an increase and decrease of the red mCherry means an increase and decrease of expression of the myosin-heavy chain IIb protein (an increase and decrease of the number of cells which express the myosin-heavy chain IIb protein). The myosin-heavy chain IIb protein is expressed in the fast-twitch fiber, and is related to the glycolytic metabolism (Table 1). The increase of the myosin-heavy chain IIb protein represents an enhancement of glycometabolism function, and an increase of lipogenesis and amino-acids synthesis.

In addition, the test substances capable of increasing the myosin-heavy chain IIb protein are useful for treating or preventing the disease associated with decrease of fast muscle. In particular, the test substances can be used as agents for preventing or treating sarcopenia, or agents for treating ALS.

Further, the test substances are useful for a selective, therapeutic transplantation of mesenchymal stem cells, muscle stem cells, and/or myoblasts for the purpose of treatment of muscle damage, muscular dystrophy, amyotrophic lateral sclerosis (ALS), disuse muscle atrophy, chronic cardiac failure, sarcopenia, autoimmune myasthenia gravis, polymyositis, dermatomyositis, inclusion body myositis, Guillain-Barré syndrome, external injury or muscle tissue reconstruction after surgery treatment. The substance capable of increasing the myosin-heavy chain IIb protein may increase cells with the myosin-heavy chain IIb fiber. In the transplantation therapy, it is important that the slow-twitch fiber cells and the fast-twitch fiber cells are inductively-differentiated from mesenchymal stem cells, muscle stem cells, and/or myoblasts, according to a property of a skeletal muscle of interest. In connection to this, the substances capable of increasing the myosin-heavy chain IIb protein can be effectively used for the differentiation induction of cells with the myosin-heavy chain IIb fiber due to the differentiation-inducing property of cells with the myosin-heavy chain IIb fiber.

TABLE 1

|  | Slow twitch fiber | Fast twitch fiber | | |
| --- | --- | --- | --- | --- |
|  | I/β | IIa | IId/x | IIb |
| Contraction rate | Slow | Fast (IIb > IId/x > IIa) | | |
| Fatigue tolerance | Good | Moderate | Poor | Poor |
| Metabolism | Oxidative | Oxidative/ Glycolytic | Oxidative/ Glycolytic | Glycolytic |
| Energy efficiency | Excellent | Moderate | Poor | Poor |
| Anatomical color | Red | Red | White | White |
| Muscle fiber size | Thin | Moderate | Thick | Thick |

Further, cellular genes or cell-producing molecules (protein) related to the metabolic shift of skeletal muscle can be discovered by using the substances involved in the metabolic shift of skeletal muscle obtained by the screening method of the present invention. A screening of such genes and molecules (proteins) from cells can be carried out using known techniques.

(Substance Involved in Metabolic Shift)

The substance involved in a metabolic shift obtainable by the screening method of the present invention may induce the differentiation of the muscle stem cells and/or myoblast to the myotube cell (muscle fiber cell). Further, the substances can also induce the differentiation of mesenchymal stem cells to muscle stem cells, myoblasts, and myotube cells (muscle fiber cells).

The mesenchymal stem cells are not particularly limited, but have a differentiation-inducing property, and can differentiate to bone cells, cardiac muscle cells, cartilage cells, tendon cells, skeletal muscle cells, adipose cells, or the like. It is considered that the mesenchymal stem cells exist in mesenchymal tissues. Bone marrow-derived mesenchymal stem cells, dental pulp-derived mesenchymal stem cells, adipose tissue-derived mesenchymal stem cells, placentaderived mesenchymal stem cells, amnion-derived mesenchymal stem cells, umbilical cord and umbilical cord blood-derived mesenchymal stem cells, can be used as the mesenchymal stem cells. The substances involved in a metabolic shift can inductively differentiate, for example, the above mesenchymal stem cells to muscle stem cells, myoblasts, and myotube cells (muscle fiber cells). Therefore, the substance involved in a metabolic shift may sometimes be a ligand, an agonist, or an antagonist. That is, in the screening method of the present invention, candidate substances capable of inducing a metabolic shift of cells other than the skeletal muscle cells can be screened.

The substances involved in a metabolic shift which are screened by the screening method of the present invention are not particularly limited, as long as it has a role in the metabolic shift, but include an agent for treating or preventing disease associated with increase of fast muscle, an agent for treating or preventing disease associated with decrease of fast muscle, an agent for treating or preventing disease associated with increase of slow muscle, or an agent for treating or preventing disease associated with decrease of slow muscle, as above. Further, there may be mentioned, an anticancer drug, an immunosuppressive agent, and an agent for treating or preventing lifestyle-related diseases.

(Screening of Diseases Associated with Increase or Decrease of Fast or Slow Muscle)

As described in Example 3, T3 (triiodothyronine) known as a substance capable of increasing fast muscle fiber of a skeletal muscle can be screened by the screening method of the present invention. That is to say, the agent for treating disease associated with decrease of fast muscle can be screened by the screening method of the present invention. Further, as shown in Example 4, IL-15 which causes type I muscle fibers to increase in the slow muscle and causes type II muscle fibers to increase in the fast muscle, can be screened by the screening method of the present invention. That is to say, agents for treating the diseases associated with decrease of slow muscle and the diseases associated with decrease of fast muscle can be screened. Further, in the screening method of the present invention, an increase and decrease of expression of slow-twitch fibers or fast-twitch fibers are directly detected, and therefore, agents for treating the disease associated with decrease of fast muscle, agents for treating disease associated with increase of fast muscle, agents for treating disease associated with increase of slow muscle, or agents for treating disease associated with decrease of slow muscle can be screened.

(Screening of Anticancer Drugs)

The method for screening substances involved in a metabolic shift of the present invention may be used as a screening of anticancer drugs.

As described in Example 3, rapamycin having an anticancer function can be screened by the screening method of the present invention. Rapamycin is an mTOR inhibitor, and exhibits an anticancer function by suppressing a mammalian target of rapamycin (hereinafter referred to as an mTOR). A cancer cell in which mTOR is constantly activated is known, and it is considered that such a cancer cell is suppressed by rapamycin. Further, rapamycin suppresses a proliferation of muscle stem cells (satellite cells), as described in Example 5. The mTOR is controlled through a receptor activated by extracellular signals (for example, insulin and insulin-like growth factors) and an intracellular serine/threonine kinase (i.e. PI3 kinase, AKT). Further, the mTOR signaling pathway is also controlled by AMP-activated protein kinase, and regulates a survival of cells and a proliferation of cells. In the screening method of the present invention, compounds capable of suppressing or enhancing several factors such as serine/threonine kinase or AMP-activated protein kinase involved in the mTOR signaling pathway, can be screened. Then, the screened compounds are expected to exhibit a function of an anticancer drug in the same way as the mTOR inhibitor. Thus, anticancer drugs other than rapamycin bound to mTOR can be screened by the screening method of the present invention. Further, anticancer drugs other than the compound showing an anticancer function related to the mTOR signaling pathway, can be screened. That is to say, the screening method of the present invention can be used for screening anticancer drugs.

(Screening of Immunosuppressive Agent)

The method for screening substances involved in a metabolic shift of the present invention may be used as a screening of immunosuppressive agents.

As described in Example 3, rapamycin having an immunosuppressive function can be screened by the screening method of the present invention. Rapamycin is an mTOR inhibitor, and exhibits an immunosuppressive function by suppressing mTOR. The mTOR is controlled through a receptor activated by extracellular signals (for example, insulin and insulin like growth factor) and an intracellular serine/threonine kinase (i.e. PI3 kinase, AKT). Further, the mTOR signaling pathway is also controlled by AMP-activated protein kinase, and regulates a survival of cells and a proliferation of cells. In the screening method of the present invention, compounds capable of suppressing or enhancing several factors such as serine/threonine kinase or AMP-activated protein kinase involved in the mTOR signaling pathway, can be screened. Then, such compounds are expected to exhibit a function of an immunosuppressive agent in the same way as the mTOR inhibitor. Thus, compounds having an immunosuppressive function other than rapamycin bound to mTOR can be screened by the screening method of the present invention. Further, immunosuppressive agents other than the compound showing an immunosuppressive function related to the mTOR signaling pathway, can be screened. That is to say, the screening method of the present invention can be used for screening immunosuppressive agents.

(Screening for Agent for Treating Lifestyle-Related Disease)

The method for screening substances involved in a metabolic shift of the present invention may be used as a screening of agents for treating a lifestyle-related disease.

As described in Examples 3 and 4, FGF21 and β3 receptor agonist (CL316243) which have a function of differentiation of a white adipocyte into a brown adipocyte, can be screened by the screening method of the present invention. The brown adipocyte can generate a large amount of heat by burning fat and sugar, compared to the white adipocyte. Thus, if the brown adipocytes are increased, the fat is consumed and it is useful for treating obesity that is a significant cause thereof. Then, if the obesity is improved, it is useful for treating lifestyle-related diseases such as diabetes, hyperpiesia, arteriosclerosis, cerebral vascular disease or cardiovascular disturbance. Therefore, FGF21 and β3 receptor agonist (CL316243) can be used as the therapeutic agents for lifestyle-related disease by differentiating white adipocytes into brown adipocytes.

Further, compounds capable of differentiating white adipocytes into brown adipocytes other than FGF21 and β3 receptor agonist (CL316243), i.e., the therapeutic agents for lifestyle-related disease, can be screened by the screening method of the present invention. That is to say, the screening method of the present invention can be used for screening therapeutic agents for lifestyle-related disease.

In addition, as shown in Example 4, IL-15 which is effective for treating obesity by decreasing visceral adipose cells can be screened by the screening method of the present invention. Thus, compounds which are effective for treating obesity by a mechanism other than the mechanism of differentiation of white adipocytes into brown adipocytes, can be screened by the screening method of the present invention.

The screening kit of the present invention can be used for the above screening method. Therefore, the screening kit of the present invention contains the muscle stem cells or myoblasts, or the inductively-differentiated myotube cells therefrom described in item "[1] Muscle stem cell or myoblast". Further, the screening kit of the present invention may contain an agent for detecting mRNA of the myosin-heavy chain I fusion gene wherein a myosin-heavy chain I gene and a fluorescent protein or photoprotein gene are fused, the myosin-heavy chain IIa fusion gene wherein a myosin-heavy chain IIa gene and a fluorescent protein or photoprotein gene are fused, the myosin-heavy chain IId/x fusion gene wherein a myosin-heavy chain IId/x gene and a fluorescent protein or photoprotein gene are fused, or the myosin-heavy chain IIb fusion gene wherein a myosin-heavy chain IIb gene and a fluorescent protein or photoprotein gene are fused. Specifically, the screening kit may contain an agent for RT-PCR, such as a probe, primers, and an enzyme.

In another embodiment, the screening kit of the present invention may contain an agent for detecting the myosin-heavy chain I protein, or the fluorescent protein or photoprotein bound thereto, the myosin-heavy chain IIa protein, or the fluorescent protein or photoprotein bound thereto, the myosin-heavy chain IId/x protein, or the fluorescent protein or photoprotein bound thereto, or the myosin-heavy chain IIb protein, or the fluorescent protein or photoprotein bound thereto. In particular, the screening kit may contain an antibody, an enzyme, and the like.

Further, the screening kit of the present invention may contain an agent for measuring the amount of the fluorescent protein or photoprotein. In particular, there may be mentioned a luciferin for luminescent reaction, or a horseradish peroxidase or alkaline phosphatase for chromogenic reaction.

The muscle stem cells or myoblasts, or the inductively-differentiated myotube cells therefrom of the present invention can be used for preparing the kit for screening substances involved in a metabolic shift. Further, the muscle stem cells or myoblasts, or the inductively-differentiated myotube cells therefrom of the present invention can be used as a tool for screening substances involved in a metabolic shift. Preferably, the substance involved in the metabolic shift is a medicine selected from a group consisting of the agent for treating or preventing diseases associated with decrease of slow muscle, the agent for treating or preventing diseases associated with increase of slow muscle, the agent for treating or preventing disease associated with decrease of fast muscle, the agent for treating or preventing disease associated with increase of fast muscle, the anticancer drug, immunosuppressive agent, and the agent for treating or preventing lifestyle-related disease.

[3] Pharmaceutical Composition (1) Pharmaceutical Composition Comprising Rapamycin or a Derivative Thereof The pharmaceutical composition for treating or preventing diseases associated with skeletal muscle weakness, muscle atrophy, or muscle damage comprises rapamycin or a derivative thereof.

Rapamycin is a compound of the formula (1):

[Chem. 1]

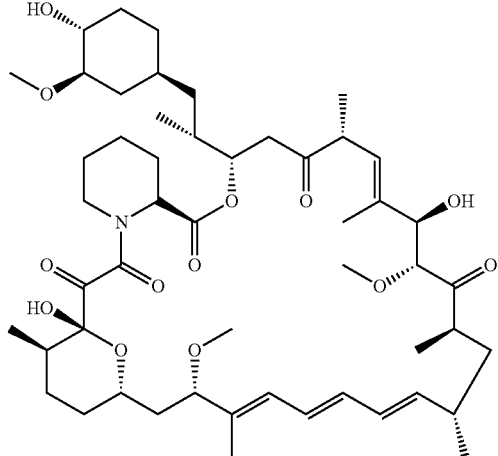

It is reported that rapamycin has an immunosuppressive effect, cancer suppressive effect, life-extending effect and a proliferation inhibition effect of a smooth muscle. However, it is not known if rapamycin causes the myosin-heavy chain I to increase and the myosin-heavy chain IIb to decrease. In addition, the pharmaceutical composition can comprise the derivative of rapamycin. The derivative of rapamycin includes ones described in the report of Seth A. Wader et al. (Journal of Clinical Investigation, 2011, (U.S.A.) vol. 121, p. 1231-41)

The disease associated with skeletal muscle weakness, muscle atrophy, or muscle damage is not particularly limited, but includes a disuse muscle atrophy, motor nerve damage, cachexia, chronic obstructive lung disease, Crohn disease, sarcopenic obesity, arteriosclerosis with muscle atrophy, muscle atrophy associated with cerebral vascular disease, type I or type II diabetic amyotrophy, muscle damage, external injury, muscular dystrophy, distal myopathy, congenital myopathy, glycogen storage disease, mitochondrial myopathy, steroid myopathy, inflammatory myopathy, endocrine myopathy, lipid storage myopathy, amyotrophic lateral sclerosis (ALS), chronic cardiac failure, sarcopenia, autoimmune myasthenia gravis, polymyositis, dermatomyositis, inclusion body myositis, Guillain-Barré syndrome, congenital myasthenia syndrome, or muscle tissue reconstruction after surgery treatment. The pharmaceutical composition comprising rapamycin can be directly used for treating or preventing disuse muscle atrophy, motor nerve damage, cachexia, chronic obstructive lung disease, Crohn disease, sarcopenic obesity, arteriosclerosis with muscle atrophy, muscle atrophy associated with cerebral vascular disease, or type I or type II diabetic amyotrophy.

Further, the pharmaceutical composition can be used for promoting the differention or proliferation of muscle stem cells and/or myoblasts in the selective, therapeutic transplantation of mesenchymal stem cells, muscle stem cells, and/or myoblasts for the purpose of treatment of muscle damage, external injury, muscular dystrophy, distal myopathy, congenital myopathy, glycogen storage disease, mitochondrial myopathy, steroid myopathy, inflammatory myopathy, endocrine myopathy, lipid storage myopathy, amyotrophic lateral sclerosis (ALS), disuse muscle atrophy, chronic cardiac failure, sarcopenia, autoimmune myasthenia gravis, polymyositis, dermatomyositis, inclusion body myositis, Guillain-Barré syndrome, congenital myasthenia syndrome, or muscle tissue reconstruction after surgery treatment. In addition, the pharmaceutical composition comprising rapamycin of the present invention is useful in conjunction with a rehabilitation therapy (exercise therapy) and a nutrition therapy.

(2) Pharmaceutical Composition Comprising Fibroblast Growth Factor 21

The pharmaceutical composition for treating or preventing diseases associated with skeletal muscle weakness, muscle atrophy, or muscle damage comprises fibroblast growth factor 21 (hereinafter, sometimes referred to as FGF21). The fibroblast growth factor 21 is a protein consisting of the amino acid sequence of SEQ ID NO: 1 or SEQ ID NO: 1, and belongs to the fibroblast growth factor family (FGF family). It is known that FGF21 exhibits a systematical effect. However, it is not known if FGF21 causes the myosin-heavy chain I to increase. In connection with this, the protein consisting of the amino acid sequence of SEQ ID NO: 1 is the mouse fibroblast growth factor 21 and the protein consisting of the amino acid sequence of SEQ ID NO: 2 is the human fibroblast growth factor 21. The fibroblast growth factor 21, which can be used as an active ingredient of the pharmaceutical composition of the present invention, is not limited to the mouse fibroblast growth factor 21 or the human fibroblast growth factor 21, so long as it has a function of a metabolic shift in the muscle stem cells. For example, the fibroblast growth factor 21 comprises a polypeptide consisting of an amino acid sequence in which one or multiple amino acids are deleted, substituted, and/or inserted in the amino acid sequence of the mouse fibroblast growth factor 21 (SEQ ID NO: 1) or the human fibroblast growth factor 21 (SEQ ID NO: 2), and exhibiting the differentiation-inducing property of cells having differentiation capacity to myotube cells to myotube cells. In particular, the fibroblast growth factor 21 of, for example, a cattle, horse, sheep, goat, rat, canine, or feline can be used.

The disease associated with skeletal muscle weakness, muscle atrophy, or muscle damage is not particularly limited, but includes a disuse muscle atrophy, motor nerve damage, cachexia, chronic obstructive lung disease, Crohn disease, sarcopenic obesity, arteriosclerosis with muscle atrophy, muscle atrophy associated with cerebral vascular disease, type I or type II diabetic amyotrophy, muscle damage, external injury, muscular dystrophy, distal myopathy, congenital myopathy, glycogen storage disease, mitochondrial myopathy, steroid myopathy, inflammatory myopathy, endocrine myopathy, lipid storage myopathy, amyotrophic lateral sclerosis (ALS), chronic cardiac failure, sarcopenia, autoimmune myasthenia gravis, polymyositis, dermatomyositis, inclusion body myositis, Guillain-Barré syndrome, congenital myasthenia syndrome, or muscle tissue reconstruction after surgery treatment. The pharmaceutical composition comprising fibroblast growth factor 21 can be directly used for treating or preventing disuse muscle atrophy, motor nerve damage, cachexia, chronic obstructive lung disease, Crohn disease, sarcopenic obesity, arteriosclerosis with muscle atrophy, muscle atrophy associated with cerebral vascular disease, or type I or type II diabetic amyotrophy.

Further, the pharmaceutical composition can be used for promoting the differential proliferation of mesenchymal stem cells, muscle stem cells and/or myoblasts in the selective, therapeutic transplantation of mesenchymal stem cells, muscle stem cells, and/or myoblasts for the purpose of treatment of muscle damage, external injury, muscular dystrophy, distal myopathy, congenital myopathy, glycogen storage disease, mitochondrial myopathy, steroid myopathy, inflammatory myopathy, endocrine myopathy, lipid storage myopathy, amyotrophic lateral sclerosis (ALS), disuse muscle atrophy, chronic cardiac failure, sarcopenia, autoimmune myasthenia gravis, polymyositis, dermatomyositis, inclusion body myositis, Guillain-Barré syndrome, congenital myasthenia syndrome, or muscle tissue reconstruction after surgery treatment. In addition, the pharmaceutical composition comprising fibroblast growth factor 21 of the present invention is expected to recover an endurance capacity of skeletal muscle, in a single administration or in conjunction with an exercise therapy and a nutrition therapy.

(3) Pharmaceutical Composition Comprising β3 Receptor Agonist or a Derivative Thereof The pharmaceutical composition for treating or preventing diseases associated with skeletal muscle weakness, muscle atrophy, or muscle damage comprises β3 receptor agonist or a derivative thereof. The β3 receptor agonist is not limited, so long as it is an agonist of β3 adrenaline receptor, but includes mirabegron or noradrenaline of the formula (2):

[Chem. 2]

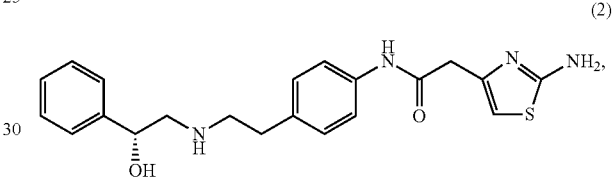

(2)

BRL37344 of the formula (3):

[Chem. 3]

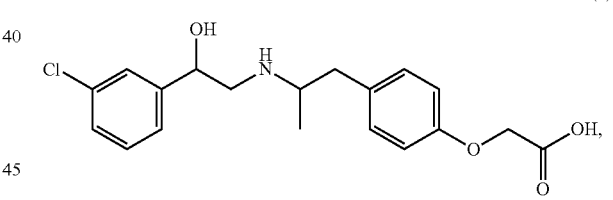

(3)

CL316243 of the formula (4):

[Chem. 4]

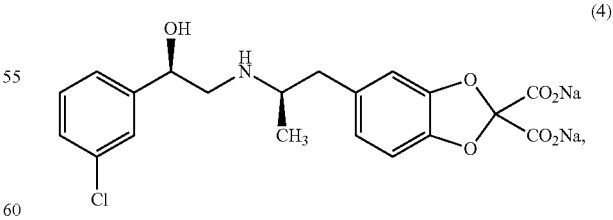

(4)

or derivatives thereof. It is considered that β3 receptor exists on adipose cells, in the digestive tract, or in the liver, and is related to a basal metabolism.

The disease associated with skeletal muscle weakness, muscle atrophy, or muscle damage is not particularly limited, but includes a disuse muscle atrophy, motor nerve damage, cachexia, chronic obstructive lung disease, Crohn disease, sarcopenic obesity, arteriosclerosis with muscle atrophy, muscle atrophy associated with cerebral vascular disease, type I or type II diabetic amyotrophy, muscle damage, external injury, muscular dystrophy, distal myopathy, congenital myopathy, glycogen storage disease, mitochondrial myopathy, steroid myopathy, inflammatory myopathy, endocrine myopathy, lipid storage myopathy, amyotrophic lateral sclerosis (ALS), chronic cardiac failure, sarcopenia, autoimmune myasthenia gravis, polymyositis, dermatomyositis, inclusion body myositis, Guillain-Barré syndrome, congenital myasthenia syndrome, or muscle tissue reconstruction after surgery treatment. The pharmaceutical composition comprising β3 receptor agonist can be directly used for treating or preventing disuse muscle atrophy, motor nerve damage, cachexia, chronic obstructive lung disease, Crohn disease, sarcopenic obesity, arteriosclerosis with muscle atrophy, muscle atrophy associated with cerebral vascular disease, or type I or type II diabetic amyotrophy.

Further, the pharmaceutical composition can be used for promoting the differential proliferation of muscle stem cells and/or myoblasts in the selective, therapeutic transplantation of mesenchymal stem cells, muscle stem cells, and/or myoblasts for the purpose of treatment of muscle damage, external injury, muscular dystrophy, distal myopathy, congenital myopathy, glycogen storage disease, mitochondrial myopathy, steroid myopathy, inflammatory myopathy, endocrine myopathy, lipid storage myopathy, amyotrophic lateral sclerosis (ALS), disuse muscle atrophy, chronic cardiac failure, sarcopenia, autoimmune myasthenia gravis, polymyositis, dermatomyositis, inclusion body myositis, Guillain-Barré syndrome, congenital myasthenia syndrome, or muscle tissue reconstruction after surgery treatment.

The formulation of the pharmaceutical composition of the present invention is not limited. However, there may be mentioned oral agents, such as powders, subtle granules, granules, tablets, capsules, suspensions, emulsions, sylups, extracts, or balls; or parentarnal agents, such as injections, liquid for external use, ointments, suppositorys, creams for local administration, or eye-drops.

The above oral agent can be prepared in accordance with conventional methods, using fillers, such as gelatin, alginate sodium, starch, cornstarch, saccharose, lactose, glucose, mannitol, carboxymethyl-cellulose, dextrin, polyvinyl pyrrolidone, clystalline cellulose, soy lecithin, sucrose, fatty acid ester, talc, magnesium stearate, polyethylene glycol, magnesium silicate, silicic anhydride, or synthetic aluminum silicate; binders, disintegrators, detergents, lubricants, flow accelerator, diluents, preservatives, colorants, flavors, correctives, stabilizers, humectants, antiseptics, antioxidant, or the like.

Examples of the parentarnal administration include injection (for example, subcutaneous injection or intravenous injection), rectal administration, or the like. Among them, the injections are preferably used.

For example, in a preparation of the injections, an aqueous solvent such as normal saline solution or Ringer solution, non-aqueous solutions such as plant oil or fatty acid ester, a tonicity agent such as glucose or sodium chloride, a solubility assisting agent, a stabilizing agent, an antiseptic agent, a suspending agent, or an emulsifying agent, may be optionally used, in addition to the active ingredient.

Further, the pharmaceutical composition of the present invention may be administered by means of sustained-release formulation using a sustained-release polymer. For example, the pharmaceutical composition of the present invention is introduced into a pellet of ethylene vinyl acetate polymer, and then the pellet can be surgically implanted into a tissue to be treated or prevented.

The pharmaceutical composition may contain, but is not limited to, 0.01 to 99% by weight, preferably 0.1 to 80% by weight, of the active ingredient.

A dose of the pharmaceutical composition of the present invention may be appropriately determined in accordance with, for example, age, sex, body weight, or degree of symptom of each patient, the type of each active ingredient, type of each disease, route of administration, or the like, and the determined dosage can be administered orally or parenterally.

In addition, dosage form for administration of the pharmaceutical composition of the present invention is not limited to a drug medicine. That is, it can be administered as a food and drink of various form, such as a functional food, a healthy food (including drink), or an animal food stuff

[4] Differentiation Inducer of Myotube Cell (1) Differentiation Inducer of Myotube Cell Comprising Rapamycin or Derivative Thereof The differentiation inducer of a myotube cell of the present invention comprises rapamycin or the derivative as an active ingredient, and can inductively differentiate the cells having myotube cell-differentiation capacity to myotube cells. As the derivatives of rapamycin, the derivatives described in item "Pharmaceutical composition" can be used.

The cells having myotube cell-differentiation capacity are not particularly limited, but include, for example, myoblasts, muscle stem cells, mesenchymal stem cells, Embryonic stem cells (ES cells), or induced pluripotent stem cells (iPS cells).

The differentiation inducer of a myotube cell of the present invention can induce the myoblasts, muscle stem cells, and/or mesenchymal stem cells in vivo, in the therapeutical transplantation of myoblasts, muscle stem cells, and/or mesenchymal stem cells to patients of, for example, muscle damage, external injury, muscular dystrophy, distal myopathy, congenital myopathy, glycogen storage disease, mitochondrial myopathy, steroid myopathy, inflammatory myopathy, endocrine myopathy, lipid storage myopathy, amyotrophic lateral sclerosis (ALS), disuse muscle atrophy, chronic cardiac failure, sarcopenia, autoimmune myasthenia gravis, polymyositis, dermatomyositis, inclusion body myositis, Guillain-Barré syndrome, congenital myasthenia syndrome, or muscle tissue reconstruction after surgery treatment. The above diseases can be treated by transplanting the induced myoblasts, muscle stem cells, and/or mesenchymal stem cells to the patient's body.

In particular, the differentiation inducer of a myotube cell comprising rapamycin exhibits an excellent slow-twitch fiber cell-inducing capacity.

(2) Differentiation Inducer of Myotube Cell Comprising Fibroblast Growth Factor 21

The differentiation inducer of a myotube cell of the present invention comprises fibroblast growth factor 21 as an active ingredient, and can inductively differentiate the cells having myotube cell-differentiation capacity to myotube cells.

The cells having myotube cell-differentiation capacity are not particularly limited, but include, for example, myoblasts, muscle stem cells, mesenchymal stem cells, Embryonic stem cells (ES cells), or induced pluripotent stem cells (iPS cells).

The differentiation inducer of a myotube cell of the present invention can induce the myoblasts, muscle stem cells, and/or mesenchymal stem cells in vivo, in the therapeutical transplantation of myoblasts, muscle stem cells, and/or mesenchymal stem cells to patients of, for example, muscle damage, external injury, muscular dystrophy, distal myopathy, congenital myopathy, glycogen storage disease, mitochondrial myopathy, steroid myopathy, inflammatory myopathy, endocrine myopathy, lipid storage myopathy, amyotrophic lateral sclerosis (ALS), disuse muscle atrophy, chronic cardiac failure, sarcopenia, autoimmune myasthenia gravis, polymyositis, dermatomyositis, inclusion body myositis, Guillain-Barré syndrome, congenital myasthenia syndrome, or muscle tissue reconstruction after surgery treatment. The above diseases can be treated by transplanting the induced myoblasts, muscle stem cells, and/or mesenchymal stem cells to the patient's body.

In particular, the differentiation inducer of a myotube cell comprising fibroblast growth factor 21 exhibits an excellent slow-twitch fiber cell-inducing capacity.

(3) Differentiation Inducer of Myotube Cell Comprising β3 Receptor Agonist or Derivative Thereof The differentiation inducer of a myotube cell of the present invention comprises β3 receptor agonist or the derivative as an active ingredient, and can inductively differentiate the cells having myotube cell-differentiation capacity to myotube cells. As the derivatives of β3 receptor agonist, the derivatives described in item "Pharmaceutical composition" can be used.

The cells having myotube cell-differentiation capacity are not particularly limited, but include, for example, myoblasts, muscle stem cells, mesenchymal stem cells, Embryonic stem cells (ES cells), or induced pluripotent stem cells (iPS cells).

The differentiation inducer of a myotube cell of the present invention can induce the myoblasts, muscle stem cells, and/or mesenchymal stem cells in vivo, in the therapeutical transplantation of myoblasts, muscle stem cells, and/or mesenchymal stem cells to patients of, for example, muscle damage, external injury, muscular dystrophy, distal myopathy, congenital myopathy, glycogen storage disease, mitochondrial myopathy, steroid myopathy, inflammatory myopathy, endocrine myopathy, lipid storage myopathy, amyotrophic lateral sclerosis (ALS), disuse muscle atrophy, chronic cardiac failure, sarcopenia, autoimmune myasthenia gravis, polymyositis, dermatomyositis, inclusion body myositis, Guillain-Barré syndrome, congenital myasthenia syndrome, or muscle tissue reconstruction after surgery treatment. The above diseases can be treated by transplanting the induced myoblasts, muscle stem cells, and/or mesenchymal stem cells to the patient's body.

In particular, the differentiation inducer of myotube cell comprising β3 receptor agonist exhibits an excellent slow-twitch fiber cell-inducing capacity.

A concentration and a reaction time of the differentiation inducer of a myotube cell of the present invention are appropriately determined in accordance with the type of cells, or a condition of culture.

EXAMPLES

The present invention will now be further illustrated by, but is by no means limited to, the following Examples.

Preparation Example 1

In this preparation example, a knock-in mouse wherein myosin heavy chain I fusion gene, a myosin heavy chain IIa fusion gene, a myosin-heavy chain IId/x fusion gene, and a myosin-heavy chain IIb fusion gene were introduced. A fusion gene of the myosin-heavy chain IIa gene and the fluorescent protein, Sirius gene, a fusion gene of the myosin-heavy chain IIb gene and the fluorescent protein mCherry gene, and a fusion gene of the myosin-heavy chain IId/x gene and the fluorescent protein, mCerulean gene, were introduced to the MyHCI-YFP knock-in mouse (National Institute of Health) wherein the fusion gene of the myosin-heavy chain I gene and fluorescent protein YFP, was introduced.

In order to prepare a targeting vector for the knock-in mouse, the BAC library of male C57BL/6J mouse, i.e., RP24-149P22 and RP24-374D24 were purchased from BACPAC Resources, and target genomic sequences of the MyHCIIa gene, MyHCIIb gene, and MyHCIId/x gene were subcloned respectively. For the subcloning of BAC sequences, a Red/ET recombination BAC subcloning kit (Gene Bridges) was used, and the genomic DNA of about 10 kb was introduced into a plasmid in which a negative selection marker (i.e., MC1-TK) is inserted. The cDNA sequences of an ultraviolet range fluorescent protein, i.e., Sirius, a red fluorescent protein, i.e., mCherry, and blue fluorescent protein, i.e., mCerulean were cloned by PCR, and they were inserted into sides of 5'-terminus of the MyHCIIa, IIb, and IId/x genes in frame of the translation initiation codon (ATG) thereof, respectively. Further, a PGK-gb2-Neomycin cassette (Gene Bridges) sandwiched by FRT sequences is inserted into the targeting vector as a positive selection marker (Table 1). The targeting vector, which was made linear, was introduced into mouse ES cells by an electroporation. After a positive selection using G418, homologous recombinant ES clones were identified by PCR and southern blotting. Then a chimeric mouse was prepared by an aggregation method using the identified ES clone, and the introduction of the fusion gene to germ-line cells was confirmed by genetically-typing offsprings obtained by crossbreeding the chimeric mouse with a male C57BL/6 mouse.

Example 1

In this Example, muscle stem cells (satellite cells) were separated from the knock-in mouse prepared in Preparation Example 1 by a negative selection and a positive selection using FACS.

To the muscles separated from the mouse, twice the amount of 0.2wt % collagenase solution was added, and the mixture was stirred for 1 hour. The mixture solution was triturated using a needle of 18 gauge, and then stirred at 37° C. for 30 minutes. The mixture solution was obtained through a cell strainer with a 40 μm pore size, and centrifuged at 1500 rpm for 10 minutes at 4° C. A supernatant was removed, and erythrocytes were hemolyzed by adding an ammonium chloride solution for removing erythrocytes to a pellet and being allowed to stand on ice for 30 seconds. PBS (2% FBS) was added thereto, and the mixture was centrifuged at 1500 rpm for 10 minutes at 4° C. A supernatant was removed, and a pellet was suspended using PBS (2% FBS, SM/C-2.6-biotin (×200)), and was allowed to stand on ice for 30 minutes. PBS (2% FBS) was added thereto, and the whole was centrifuged at 1500 rpm for 5 minutes at 4° C. A supernatant was removed, and a pellet was suspended using PBS (2% FBS, CD31-FITC (×400), CD45-FITC (×800), Sca1-PE (×400), Streptavidin-APC (×400)). After being allowed to stand on ice for 30 minutes, PBS (2% FBS) was added to the suspension, and the whole was centrifuged at 1500 rpm for 5 minutes at 4° C. A supernatant was removed, and a pellet was suspended using PBS (2% FBS). The suspension was get obtained through a cell strainer, and 1 mg/mL of PI (×500) was added thereto. Muscle stem cells (satellite cells) were separated by analysis using FACS.

Example 2

In this Example, immortalized cells of the muscle stem cells (satellite cells) were obtained. In order to obtain the immortalized cells, the Immortmouse having an H-2Kb-promoter and a temperature-sensitive SV40 large T antigen inducible by IFN-γ, was used. In the Immortmouse, an SV40 large T antigen is expressed by IFN-γ, and an immortalization of a cell can be induced.

The knock-in mouse prepared in Preparation Example 1 and the Immortmouse were crossbred to obtain offspring. Muscle stem cells (satellite cells) were separated from the obtained offspring in accordance with the method of Example 1. An immortalization of the separated muscle stem cells was induced by culturing the same at 33° C., in the presence of 10 ng/mL of IFN-γ. The temperature-sensitive SV40 large T antigen was degraded by culturing the resulting cells at 37° C., to obtain the immortalized muscle stem cells (satellite cells).

In this Example, 27 test compounds were tested by the screening method of substances involved in a metabolic shift using the immortalized muscle stem cells (satellite cells) prepared in Example 2.

Figure 3:
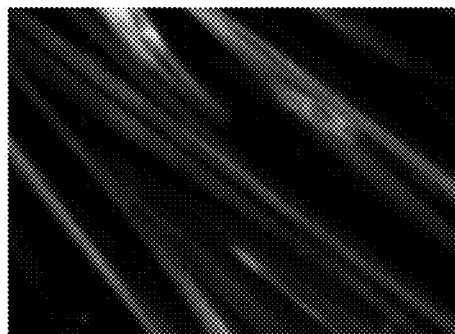
FIG. 3 is a photograph showing myotube cells in which YFP bound to myosin heavy chain I gene is expressed, and myotube cells in which Sirius bound to myosin heavy chain IIa gene is expressed (A), and a photograph showing myotube cells in which mCerulean bound to a myosin-heavy chain IId/x gene is expressed and myotube cells in which mCherry bound to a myosin-heavy chain IIb gene is expressed (B).
Figure 3:
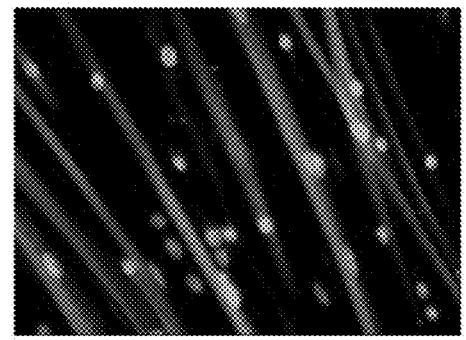

The immortalized muscle stem cells ($1\times10^5$) were seeded on a 60 mm dish or the immortalized muscle stem cells ($2\times10^3$) were seeded on a 96 well plate. The cells were cultured in a DMEM containing 20% FBS, bFGF (10 ng/mL), and IFNy (10 ng/mL) at 33° C. for 1 day, and then, cultured in a DMEM containing 5% HS at 37° C. for 3 days. Subsequently, test substances were serially diluted by a DMEM containing 5% horse serum at an appropriate dilution rate, and the diluted substances were added to the dishes respectively. After two days treatment, fluorescences of YFP, Sirius, mCherry, and mCerulean in the living cells were observed using a fluorescence microscope, and the number of cells, which generate the respective fluorescence, was measured. FIG. 3A shows the photographs of myotube cells in which YFP bound to a myosin-heavy chain I gene was expressed, and myotube cells in which Sirius bound to a myosin-heavy chain IIa gene is expressed. FIG. 3B shows the photographs of myotube cells in which mCerulean is bound to a myosin-heavy chain IId/x gene was expressed and myotube cells in which mCherry is bound to a myosin-heavy chain IIb gene was expressed.

Figure 4:
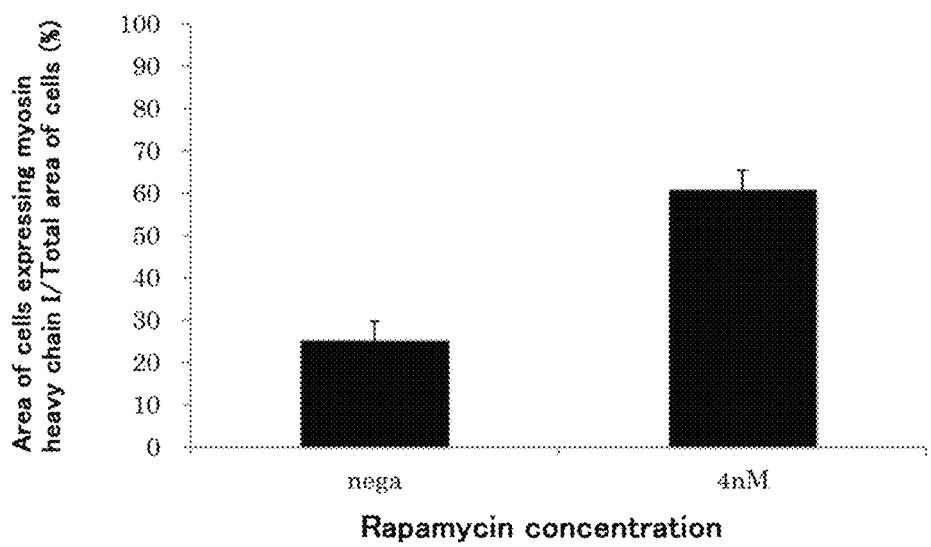
FIG. 4 is a set of graphs showing that cells expressing a myosin-heavy chain I protein are increased by adding rapamycin (A), and cells expressing a myosin-heavy chain IIb protein are decreased by adding rapamycin (B).
Figure 4:
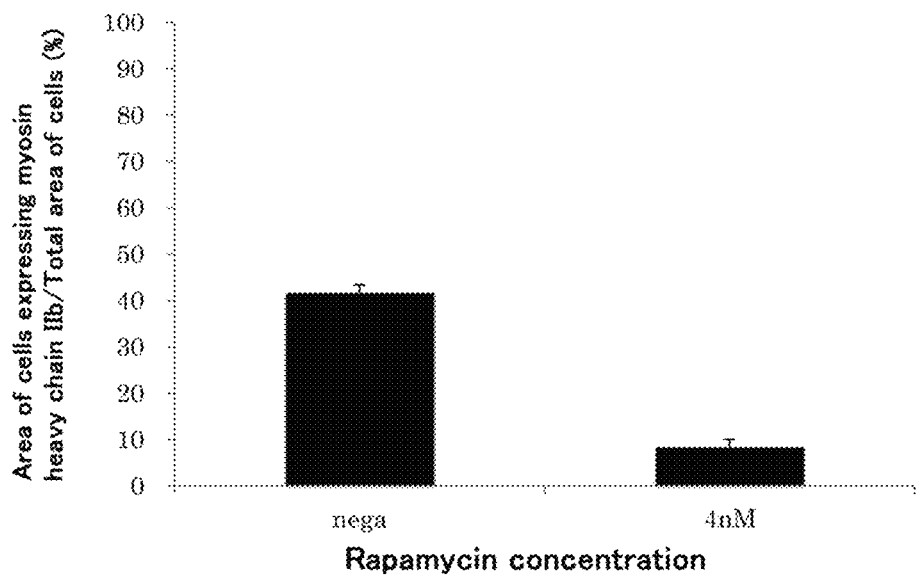

In the screening method, one of the test substances, i.e., rapamycin increased the cells expressing the myosin-heavy chain I protein and decreased the cells expressing the myosin-heavy chain IIb protein. The results of rapamycin were shown in FIG. 4. The term "nega" means a negative control in which rapamycin was not added. Compared to the negative control, the rapamycin increased the number of myotube cells that generate fluorescence of YFP, and decreased the number of myotube cells that generate fluorescence of mCherry. Specifically, an area of cells expressing the myosin-heavy chain I protein was increased from 25.3% to 60.9%, and an area of cells expressing the myosin-heavy chain IIb protein was decreased from 41.8% to 8.4% by bringing the myotube cells into contact with 4 nM of rapamycin.

That is to say, rapamycin can improve a metabolic function of skeletal muscle, and thus can be used as the agent for treating diseases associated with skeletal muscle weakness, muscle atrophy, or muscle damage. In particular, rapamycin is useful as the agent for treating the disease associated with a decrease of slow muscle.

Figure 5:
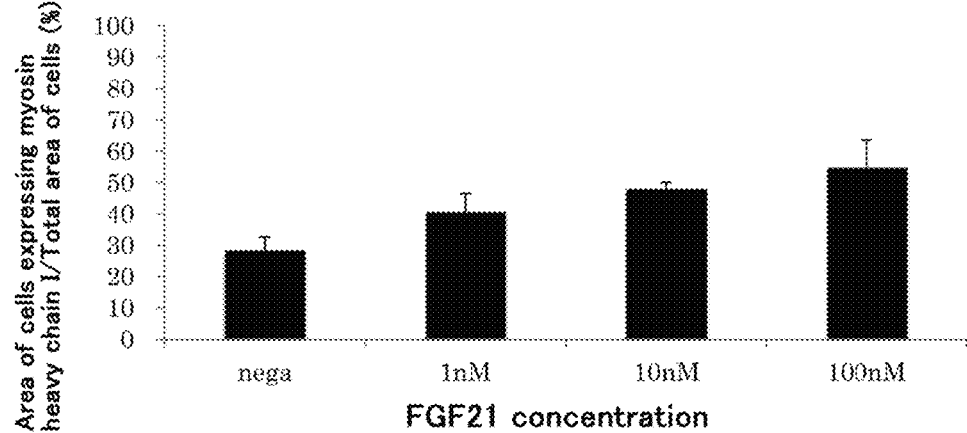
FIG. 5 is a graph showing that cells expressing a myosin-heavy chain I protein are increased by adding fibroblast growth factor 21.

Further, in the screening method, one of the test substances, i.e., mouse fibroblast growth factor 21 (FGF21) increased the cells expressing the myosin-heavy chain I protein. The results of FGF21 were shown in FIG. 5. The term "nega" means a negative control in which the mouse fibroblast growth factor 21 (FGF21) was not added. Compared to the negative control, the fibroblast growth factor 21 increased the number of myotube cells that generate fluorescence of YFP. However, the number of myotube cells that generate fluorescence of mCherry remains static by the FGF21. Specifically, an area of cells expressing the myosin-heavy chain I protein was increased from 28.4% to 40.6%, 48.0% and 54.9%, by bringing the myotube cells into contact with 1 nM, 10 nM, and 100 nM of mouse fibroblast growth factor 21, respectively.

That is to say, FGF21 can improve a metabolic function of skeletal muscle, and thus can be used as the agent for treating diseases associated with skeletal muscle weakness, muscle atrophy, or muscle damage. In particular, FGF21 is useful as the agent for treating the disease associated with a decrease of slow muscle.

Figure 6:
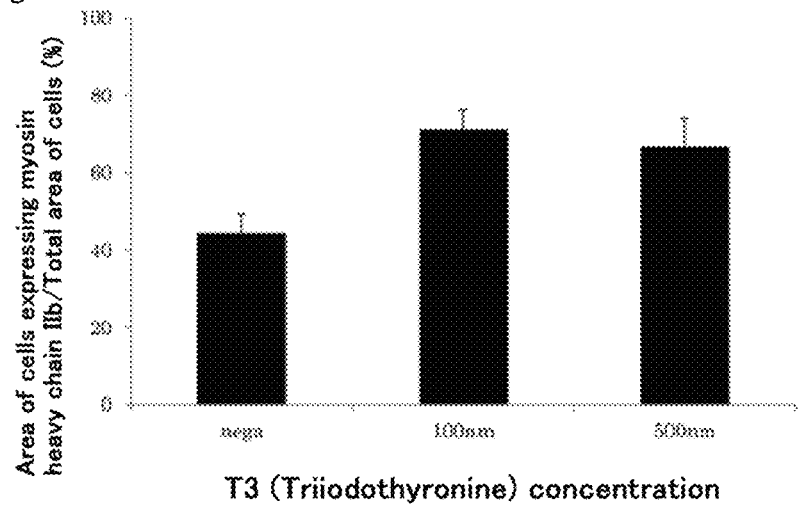
FIG. 6 is a graph showing that cells expressing a myosin-heavy chain IIb protein are increased by adding T3 (triiodothyronine).

Furthermore, one of the test substances, i.e., T3 (triiodothyronine) increased the cells expressing the myosin-heavy chain IIb protein. The results of T3 were shown in FIG. 6. An area of cells expressing the myosin-heavy chain IIb protein was increased from 44.5% to 71.3%, and 70.0%, by bringing the myotube cells into contact with 100 nM, and 500 nM of T3(triiodothyronine), respectively. That is to say, T3 can improve a metabolic function of skeletal muscle, and thus can be used as the agent for treating diseases associated with skeletal muscle weakness, muscle atrophy, or muscle damage. In particular, T3 is useful as the agent for treating the disease associated with a decrease of fast muscle. It is known that T3 (triiodothyronine) increases the fast muscle fiber of skeletal muscle. The results of this Example are consistent with well-known knowledge, and therefore, show that the screening system of the present invention is useful.

Example 4

In this example, additional test compounds were tested using the immortalized muscle stem cells (satellite cells) prepared in Example 2. The screening method of substances involved in a metabolic shift was performed by repeating a procedure of Example 3.

Figure 7:
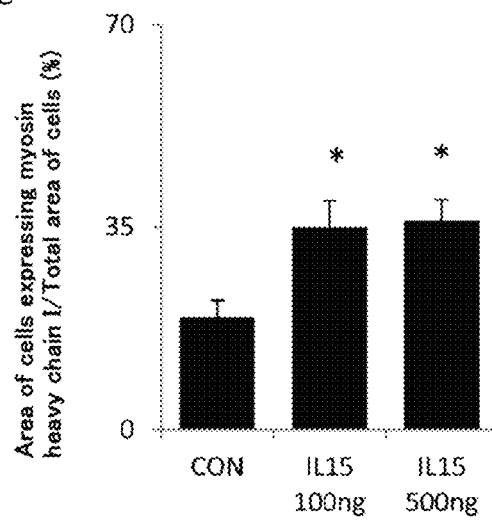
FIG. 7 is a set of graphs showing that cells expressing a myosin-heavy chain I protein are increased by adding IL-15, and cells expressing a myosin-heavy chain IIb protein are increased by adding IL-15.
Figure 7:
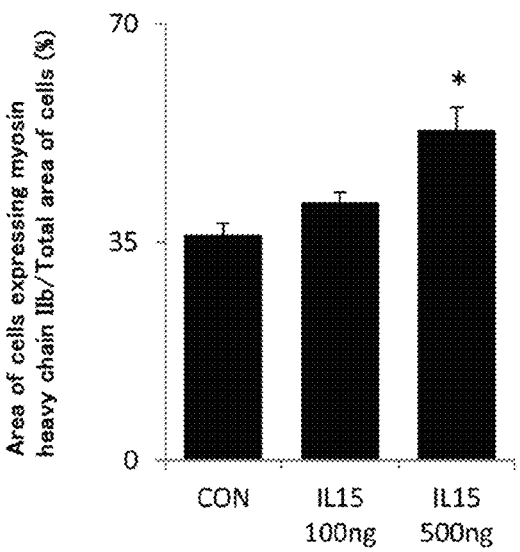

In the screening method, one of the test substances, i.e., IL-15 increased the cells expressing the myosin-heavy chain I protein, and increased the cells expressing the myosin-heavy chain III) protein. The results of IL-15 were shown in FIG. 7. The term "nega" means a negative control in which the IL-15 was not added. Compared to the negative control, the IL-15 increased the number of myotube cells that generates fluorescence of YFP and increased the number of myotube cells that generates fluorescence of mCherry. Specifically, an area of cells expressing the myosin-heavy chain I protein was increased from 19.5% to 35.0% or 36.1%, by bringing the myotube cells into contact with 100 ng/mL or 500 ng/mL of IL-15, respectively, and an area of cells expressing the myosin-heavy chain IIb protein was increased from 36.2% to 53.0% by bringing the myotube cells into contact with 500 ng/mL of IL-15.

That is to say, IL-15 can improve a metabolic function of skeletal muscle, and thus can be used as the agent for treating diseases associated with skeletal muscle weakness, muscle atrophy, or muscle damage. In particular, IL-15 is useful as the agent for treating the disease associated with a decrease of slow muscle and/or fast muscle.

Figure 8:
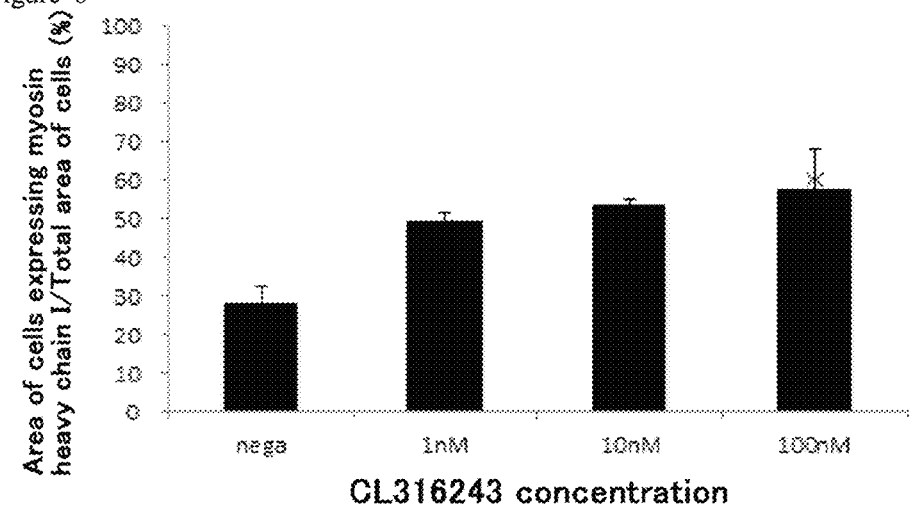
FIG. 8 is a graph showing that cells expressing a myosin-heavy chain I protein are increased by adding β3 receptor agonist (CL316243).

Further, in the screening method, one of the test substances, i.e., β3 receptor agonist (CL316243) increased the cells expressing the myosin-heavy chain I protein. The results of CL316243 were shown in FIG. 8. The term "nega" means a negative control in which the β3 receptor agonist (CL316243) was not added. Compared to the negative control, the β3 receptor agonist (CL316243) increased the number of myotube cells that generate fluorescence of YFP. However, the number of myotube cells that generate fluorescence of mCherry remains static by the β3 receptor agonist (CL316243). Specifically, an area of cells expressing the myosin-heavy chain I protein was increased from 28.4% to 49.3%, 53.8% and 57.8%, by bringing the myotube cells into contact with 1 nM, 10 nM and 100 nM of β3 receptor agonist (CL316243), respectively.

That is to say, β3 receptor agonist can improve a metabolic function of skeletal muscle, and thus can be used as the agent for treating diseases associated with skeletal muscle weakness, muscle atrophy, or muscle damage. In particular, β3 receptor agonist is useful as the agent for treating the disease associated with a decrease of slow muscle.

Example 5

The rapamycin was obtained by the metabolic shift screening method in Example 3. In this Example, whether or not the rapamycin can be screened by the proliferation inhibition screening method using satellite cells was examined.

Figure 9:
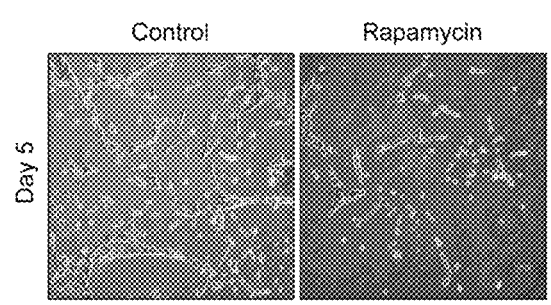
FIG. 9 is a photograph (A) and a graph (B) showing that a proliferation of satellite cells is suppressed by adding rapamycin.
Figure 9:
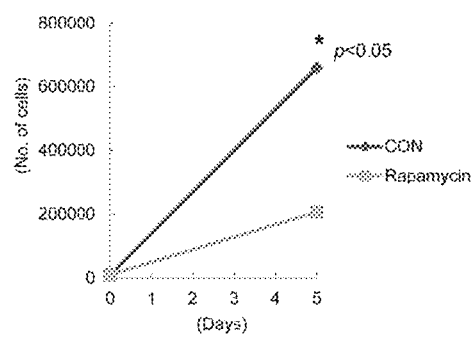

The immortalized muscle stem cells ($1 \times 10^4$) were seeded on a 35 mm dish. The cells were cultured in a DMEM containing 20% FBS, bFGF (10ng/mL), and IFNγ (10 ng/mL) at 33° C. for 1 day, and then the rapamycin was diluted to a concentration of 5 nM by a DMEM containing 5% FBS, and the diluted rapamycin was added to the dish. The number of cells was counted after five days of culturing. FIG. 9 shows a micrograph of the immortalized muscle stem cells after 5 days of culturing (A) and a graph showing that the number of cells was increased (B). The term "Control" means negative control in which the rapamycin was not added. The proliferation of satellite cells was inhibited by adding rapamycin.

INDUSTRIAL APPLICABILITY

The the substances involved in the metabolic shift of the skeletal muscle can be screened by the screening method using the muscle stem cell or myoblast of the present invention. Therefore, the agents for treating or preventing the diseases associated with skeletal muscle weakness or muscle atrophy can be screened thereby. Further, the screening method of the present invention can be used as the method for screening of an anticancer drug, immunosuppressive agents, or agents for treating or preventing lifestyle-related disease.

Although the present invention has been described with reference to specific embodiments, various changes and modifications obvious to those skilled in the art are possible without departing from the scope of the appended claims.

The invention claimed is:

1. A muscle stem cell or myoblast comprising at least one myosin-heavy chain fusion gene selected from the group consisting of:
 a myosin-heavy chain I gene and a fluorescent protein or photoprotein gene,
 a myosin-heavy chain IIa gene and a fluorescent protein or photoprotein gene,
 a myosin-heavy chain IIdix gene and a fluorescent protein or photoprotein gene, and
 a myosin-heavy chain IIb gene and a fluorescent protein or photoprotein gene.

2. The muscle stem cell or myoblast according to claim 1, wherein the cell is an immortalized cell.

3. The muscle stem cell or myoblast according to claim 1, wherein the fluorescent protein or photoprotein gene is linked 5' to the myosin heavy chain I, IIa, IIdx, or IIb gene.

4. The muscle stem cell or myoblast according to claim 1, wherein the fluorescent protein or photoprotein gene encodes at least one fluorescent protein or photoprotein selected from the group consisting of Sirius, EBFP, SBP2, ESP2, Azurite, mKalama1, TagBFP, mBlueberry, mTurquoise, ECFP, Cerulean, mCerulean, TagCFP, AmCyan, mTP1, MiCy (Midoriishi Cyan), TurboGFP, CFP, AcGFP, TagGFP, AG (Azami-Green), mAG1, ZsGreen, EmGFP (Emerald), EGFP, GP2, T-Sapphire, HyPer, TagYFP, mAmetrine, EYFP, YFP, Venus, Citrine, PhiYFP, PhiYFP-m, turboYFP, ZsYellow, mBanana, mKO1, KO(Kusabira Orange), mOrange, mOrange2, mKO2, Keima570, TurboRFP, DsRed-Express, DsRed, DsRed2, TagRFP, TagRFP-T, DsRed-Monomer, mApple, AsRed2, mStrawberry, TurboFP602, mRP1, JRed, KillerRed, mCherry, KeimaRed, HcRed, mRasberry, mKate2, TagFP635, mPlum, egFP650, Neptune, mNeptune, egFP670, and luciferase.

5. A method for screening a test substance affecting myosin heavy chain expression, said method comprising the steps of:
   a) providing a muscle stem cell or myoblast comprising at least one myosin-heavy chain fusion gene selected from the group consisting of:
   a myosin-heavy chain I gene and a fluorescent protein or photoprotein gene,
   a myosin-heavy chain IIa gene and a fluorescent protein or photoprotein gene,
   a myosin-heavy chain IId/x gene and a fluorescent protein or photoprotein gene. and
   a myosin-heavy chain IIb gene and a fluorescent protein or photoprotein gene;
   b) contacting said muscle stem cell or myoblast with a test substance; and
   c) analyzing the expression of at least one myosin-heavy chain fusion gene in said muscle stem cell or myoblast;
   wherein an increase in myosin-heavy chain fusion gene expression indicates that the test substance increases myosin heavy chain gene expression, or a decrease in myosin-heavy chain fusion gene expression indicates that the test substance decreases myosin heavy chain gene expression.

* * * * *

UNITED STATES PATENT AND TRADEMARK OFFICE
CERTIFICATE OF CORRECTION

PATENT NO. : 9,618,502 B2
APPLICATION NO. : 15/031491
DATED : April 11, 2017
INVENTOR(S) : Kazuhiro Shigemoto It is certified that error appears in the above-identified patent and that said Letters Patent is hereby corrected as shown below:

In the Claims

Column 31, Line 62: Claim 1, Delete "IIdix" and insert --IId/x--

Column 31, Line 64: Claim 1, Delete "Hb" and insert --IIb--

Column 33, Line 17: Claim 5, Delete "I1d/x" and insert --IId/x--

Signed and Sealed this
Twentieth Day of June, 2017

Joseph Matal
*Performing the Functions and Duties of the*
*Under Secretary of Commerce for Intellectual Property and*
*Director of the United States Patent and Trademark Office*